United States Patent
Brooksby et al.

(10) Patent No.: US 9,974,111 B1
(45) Date of Patent: May 15, 2018

(54) ESTABLISHMENT OF COMMUNICATION BETWEEN DEVICES

(71) Applicant: Sorenson IP Holdings, LLC, Salt Lake City, UT (US)

(72) Inventors: Scot Lorin Brooksby, Highland, UT (US); Adam Montero, Midvale, UT (US); Merle Lamar Walker, III, Sandy, UT (US)

(73) Assignee: SORENSON IP HOLDINGS, LLC, Salt Lake City, UT (US)

( * ) Notice: Subject to any disclaimer, the term of this patent is extended or adjusted under 35 U.S.C. 154(b) by 0 days. days.

(21) Appl. No.: 15/400,671

(22) Filed: Jan. 6, 2017

(51) Int. Cl.
*H04M 3/00* (2006.01)
*H04W 76/02* (2009.01)
*H04W 4/00* (2018.01)
*A61B 5/00* (2006.01)
*A61B 5/0205* (2006.01)
*A61B 5/021* (2006.01)
*A61B 5/08* (2006.01)

(52) U.S. Cl.
CPC .......... *H04W 76/14* (2018.02); *A61B 5/0022* (2013.01); *A61B 5/0205* (2013.01); *A61B 5/02055* (2013.01); *H04W 4/008* (2013.01); *H04W 4/80* (2018.02); *H04W 76/023* (2013.01); *A61B 5/021* (2013.01); *A61B 5/0816* (2013.01)

(58) Field of Classification Search
CPC . A61B 5/0002; A61B 5/0022; G08B 21/0211; H04L 67/12; A61N 1/37282
USPC ........................................................ 455/418
See application file for complete search history.

(56) References Cited

U.S. PATENT DOCUMENTS

| | | |
|---|---|---|
| 5,390,238 A | 2/1995 | Kirk et al. |
| 5,434,611 A | 7/1995 | Tamura |
| 5,441,047 A | 8/1995 | David et al. |
| 5,619,991 A | 4/1997 | Sloane |
| 5,897,493 A | 4/1999 | Brown |
| 5,997,476 A | 12/1999 | Brown |
| 6,024,699 A | 2/2000 | Surwit et al. |
| 6,046,761 A | 4/2000 | Echerer |
| 6,168,563 B1 | 1/2001 | Brown |

(Continued)

FOREIGN PATENT DOCUMENTS

| | | |
|---|---|---|
| WO | 2005101276 A1 | 1/2006 |
| WO | 2012109984 A1 | 8/2012 |

(Continued)

*Primary Examiner* — Simon Nguyen
(74) *Attorney, Agent, or Firm* — Maschoff Brennan

(57) ABSTRACT

A method to establish communication between devices is provided. The method may include obtaining a request from a user at a first device to establish a communication session through a communication system over a wide area network with a second device. The communication session may provide for verbal communication between the user of the first device and a second user of the second device. The method may further include obtaining, at the first device over a local area network, current vital sign data of the user from a medical device configured to obtain vital sign data of the user. In response to the request from the user, the method may include sending a communication request to the communication system over the wide area network to establish the communication session and sending the current vital sign data to the communication system over the wide area network.

20 Claims, 19 Drawing Sheets

(56) References Cited

U.S. PATENT DOCUMENTS

| | | | |
|---|---|---|---|
| 6,256,613 B1 | 7/2001 | Falchuk et al. | |
| 6,270,457 B1 | 8/2001 | Bardy | |
| 6,364,834 B1 | 4/2002 | Reuss et al. | |
| 6,850,889 B1 | 2/2005 | Zayas, Jr. | |
| 6,980,958 B1 | 12/2005 | Surwit et al. | |
| 7,181,505 B2 * | 2/2007 | Haller | A61B 5/0031 607/32 |
| 7,603,282 B2 | 10/2009 | Imai et al. | |
| 7,739,130 B2 | 6/2010 | Surwit et al. | |
| 7,756,722 B2 | 7/2010 | Levine et al. | |
| 7,965,309 B2 | 6/2011 | Mattila et al. | |
| 8,279,061 B2 | 10/2012 | Soliman | |
| 8,423,383 B2 | 4/2013 | Koren et al. | |
| 8,817,966 B2 | 8/2014 | Wrench | |
| 9,471,751 B1 | 10/2016 | Kahn et al. | |
| 9,485,462 B2 | 11/2016 | Wrench | |
| 9,490,993 B1 | 11/2016 | Wrench | |
| 2008/0319784 A1 | 12/2008 | Cordero | |
| 2009/0058635 A1 * | 3/2009 | LaLonde | A61N 1/37282 340/539.11 |
| 2009/0259492 A1 | 10/2009 | Cossman | |
| 2011/0107253 A1 | 5/2011 | Levine et al. | |
| 2011/0167133 A1 * | 7/2011 | Jain | H04L 67/12 709/219 |
| 2011/0301429 A1 | 12/2011 | Henke | |
| 2012/0191464 A1 | 7/2012 | Stuart et al. | |
| 2012/0242501 A1 * | 9/2012 | Tran | A61B 5/0024 340/870.02 |
| 2013/0060576 A1 | 3/2013 | Hamm et al. | |
| 2013/0184540 A1 | 7/2013 | Boschetti Sacco et al. | |
| 2013/0218582 A1 | 8/2013 | LaLonde | |
| 2013/0275155 A1 | 10/2013 | Mikko | |
| 2014/0032244 A1 | 1/2014 | Kolls et al. | |
| 2014/0122107 A1 | 5/2014 | Malven et al. | |
| 2014/0122125 A1 | 5/2014 | Deshpande et al. | |
| 2014/0156299 A1 | 6/2014 | Malven et al. | |
| 2014/0276552 A1 | 9/2014 | Nguyen, Jr. | |
| 2014/0330579 A1 | 11/2014 | Cashman et al. | |
| 2015/0220695 A1 | 8/2015 | Radcliffe et al. | |
| 2015/0261918 A1 | 9/2015 | Thornbury, Jr. | |
| 2015/0261930 A1 | 9/2015 | Espinosa Escalona et al. | |
| 2015/0288797 A1 * | 10/2015 | Vincent | H04M 1/72538 455/404.2 |
| 2015/0294079 A1 * | 10/2015 | Bergougnan | G06F 19/3456 705/2 |
| 2015/0302539 A1 * | 10/2015 | Mazar | G08B 21/0211 705/3 |
| 2016/0116339 A1 * | 4/2016 | Crawley | H04W 80/04 340/573.1 |
| 2016/0188829 A1 | 6/2016 | Southerland et al. | |
| 2016/0188830 A1 | 6/2016 | Haq | |
| 2016/0344745 A1 * | 11/2016 | Johnson | H04L 67/34 |
| 2017/0262604 A1 * | 9/2017 | Francois | G06F 19/3418 |

FOREIGN PATENT DOCUMENTS

| | | |
|---|---|---|
| WO | 2012127281 A1 | 9/2012 |
| WO | 2014063162 A1 | 4/2014 |
| WO | 2015164787 A1 | 10/2015 |
| WO | 2016144784 A1 | 10/2015 |
| WO | 2016130532 A1 | 5/2016 |
| WO | 2016109820 A1 | 7/2016 |

* cited by examiner

ESTABLISHMENT OF COMMUNICATION BETWEEN DEVICES

FIELD

The embodiments discussed herein are related to establishment of communication between devices.

BACKGROUND

Communication systems allow participates in different locations to communicate. The communication media used by different communication systems may vary. For example, in some circumstances, communication media in a communication system may be written, audio, video, or some combination thereof. Different communication systems may provide varying levels of user experiences and may require different levels of user interaction.

The subject matter claimed herein is not limited to embodiments that solve any disadvantages or that operate only in environments such as those described above. Rather, this background is only provided to illustrate one example technology area where some embodiments described herein may be practiced.

SUMMARY

A method to establish communication between devices is provided. The method may include obtaining a request from a user at a first device to establish a communication session through a communication system over a wide area network with a second device. The communication session may provide for verbal communication between the user of the first device and a second user of the second device. The method may further include obtaining, at the first device over a local area network, current vital sign data of the user from a medical device configured to obtain vital sign data of the user. In response to the request from the user, the method may include sending a communication request to the communication system over the wide area network to establish the communication session. Furthermore, in response to the request from the user, the method may include sending the current vital sign data to the communication system over the wide area network.

The objects and advantages of the embodiments will be realized and achieved at least by the elements, features, and combinations particularly pointed out in the claims. Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
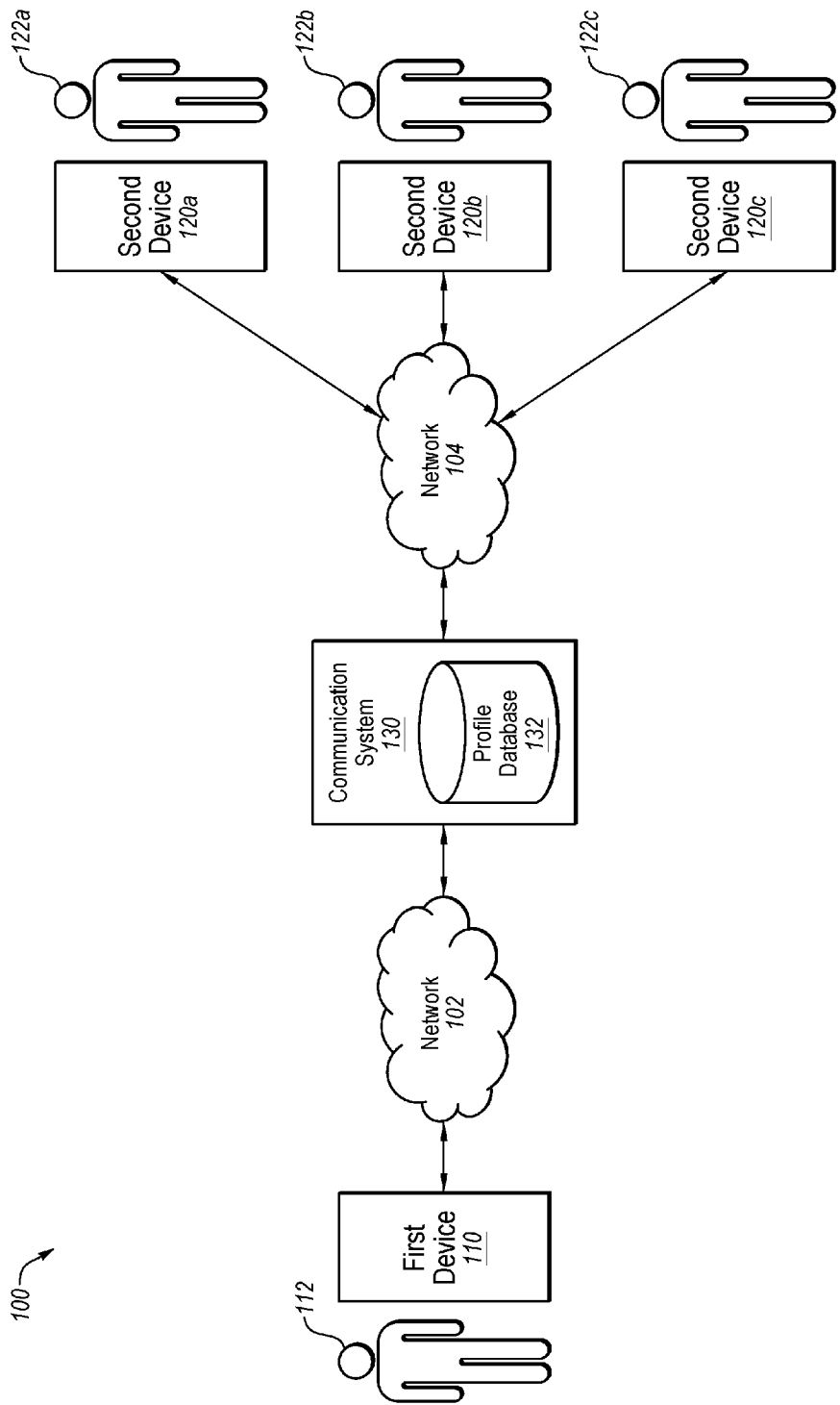
FIG. 1 illustrates an example environment related to device to device communication.

Some embodiments of the present disclosure relate to a communication system configured to establish communication sessions between devices to allow communication between users of the devices. In some embodiments, the present disclosure relates to establishing communication sessions, such as video communication sessions, between users and health care professionals. In these and other embodiments, the communication system may be configured to connect users that are in their homes with health care professionals.

In some embodiments, the communication system may obtain information about a user, such as a medical condition, through an initial process. After providing the information, a user may request a communication session with a health care professional through the communication system. The communication system may access the previously obtained information to select for the communication session an appropriate health care professional, such as a health care professional with a background suited to care for the medical condition of the user. In this manner, the communication system may reduce the information provided by a user at the time of the request. As a result, in some embodiments, a user may establish a communication session with an appropriate health care professional by selecting a single button and without providing additional information or input at the time of establishing the communication session.

In some embodiments, the communication system may be further configured to obtain current vital sign data of the user. In these and other embodiments, a user device for the communication session may communicate with a medical device configured to generate vital sign data. Upon receipt of a request for a communication session, the user device may obtain current vital sign data from the medical device and provide the current vital sign data to the communication system. The communication system may use the current vital sign data of the user to select an appropriate health care professional or to direct the communication request to an emergency response agency.

In some embodiments, the communication system may be further configured to obtain a transcription of what is said, e.g. verbally communicated, by a health care professional during a communication session. The communication system may provide the transcription of the verbal communication to the user in real-time or substantially real-time with audio of the verbal communication that is transcribed. As a result, a user may be able to read the transcription to confirm an understanding of the verbal communication of the health care professional during the communication session and after the communication session. In some embodiments, the communication system may use the previous transcripts of the communication session to select an appropriate health care professional when a later request for a communication session is submitted in the future by the user.

In short, the present disclosure provides solutions to problems in networking, telecommunications, and other technologies to enhance communications between users and health care professionals. Embodiments of the present disclosure are explained in further detail below with reference to the accompanying drawings.

Turning to the figures, FIG. 1 illustrates an example environment 100 related to device to device communication. The environment 100 may be arranged in accordance with at least one embodiment described in the present disclosure. The environment 100 may include a first network 102; a second network 104; a first device 110; a first user 112; second devices 120, including a first second-device 120a, a second second-device 120b, and a third second-device 120c; second users 122, including a first second-user 122a, a second second-user 122b, and a third second-user 122c; and a communication system 130 that includes a profile database 132.

The first network 102 may be configured to communicatively couple the first device 110 and the communication system 130. The second network 104 may be configured to communicatively couple the second devices 120 and the communication system 130.

In some embodiments, the first and second networks 102 and 104 may each include any network or configuration of networks configured to send and receive communications between devices. In some embodiments, the first and second networks 102 and 104 may each include a conventional type network, a wired or wireless network, and may have numerous different configurations. Furthermore, the first and second networks 102 and 104 may each include a local area network (LAN), a wide area network (WAN) (e.g., the Internet), or other interconnected data paths across which multiple devices and/or entities may communicate.

In some embodiments, the first and second networks 102 and 104 may each include a peer-to-peer network. The first and second networks 102 and 104 may also each be coupled to or may include portions of a telecommunications network for sending data in a variety of different communication protocols. In some embodiments, the first and second networks 102 and 104 may each include Bluetooth® communication networks or cellular communication networks for sending and receiving communications and/or data. The first and second networks 102 and 104 may also each include a mobile data network that may include third-generation (3G), fourth-generation (4G), long-term evolution (LTE), long-term evolution advanced (LTE-A), Voice-over-LTE ("VoLTE") or any other mobile data network or combination of mobile data networks. Further, the first and second networks 102 and 104 may each include one or more IEEE 802.11 wireless networks. In some embodiments, the first and second networks 102 and 104 may be configured in a similar manner or a different manner. In some embodiments, the first and second networks 102 and 104 may share various portions of one or more networks. For example, each of the first and second networks 102 and 104 may include the Internet or some other network.

The first device 110 may be any electronic or digital device. For example, the first device 110 may include or may be included in a desktop computer, a laptop computer, a smartphone, a mobile phone, a tablet computer, a television set-top box, a smart television, or any other electronic device with a processor. In some embodiments, the first device 110 may include computer-readable-instructions stored on one or more computer-readable media that are configured to be executed by one or more processors in the first device 110 to perform operations described in this disclosure.

The first device 110 may be configured to communicate, receive data from and direct data to, the communication system 130. Alternatively or additionally, the first device 110 may be configured to participate in a communication session with one or more of the second devices 120 through the communication system 130.

In some embodiments, the first device 110 may be associated with the first user 112. The first device 110 may be associated with the first user 112 based on the first device 110 being configured to be used by the first user 112. For example, the first device 110 may have settings or other configuration profiles that are set for the first user 112. In these and other embodiments, the first user 112 may be registered with the communication system 130. The registration of the first user 112 may include a device that may be used by the first user 112 in communication sessions and the first device 110 may be listed in the registration of the first user 112. Alternatively or additionally, the first device 110 may be associated with the first user 112 by the first user 112 being the owner of the first device 110 and/or being controlled by the first user 112. For example, the first device 110 may be controlled by the first user 112 when the first device 110 is obtaining commands and input from the first user 112.

In these and other embodiments, a request to participate in a communication session generated by the first device 110 may be initiated by the first user 112. During a communication session, audio and/or video may be presented by the first device 110 for the first user 112. Alternatively or additionally, a transcription of the audio presented by the first device 110 during a communication session may be presented by the first device 110 for the first user 112 during the communication session. In some embodiments, during a communication session with another device, such as one of the second devices 120, audio and video of the first user 112 may be captured by the first device 110 and provided to the other device.

In some embodiments, information about the first user 112 may be associated with the first device 110. For example, through the association of the first user 112 with the first device 110, information about the first user 112 in the communication system 130 may be associated with the first device 110. In these and other embodiments, devices selected for communication sessions with the first device 110 may be selected based on information about the first user 112.

The second devices 120 may be any electronic or digital devices. For example, the second devices 120 may include or may be included in a desktop computer, a laptop computer, a smartphone, a mobile phone, a tablet computer, a television set-top box, a smart television, or any other electronic device with a processor. In some embodiments, the second devices 120 may each include or be included in the same, different, or combinations of electronic or digital devices.

In some embodiments, the second devices 120 may each include computer-readable-instructions stored on one or more computer-readable media that are configured to be executed by one or more processors in the second devices 120 to perform operations described in this disclosure.

The second devices 120 may each be configured to communicate, receive data from and direct data to, the communication system 130. Alternatively or additionally, each of the second devices 120 may be configured to individually or in a group participate in a communication session with the first device 110 through the communication system 130.

In some embodiments, the second devices 120 may each be associated with one of the second users 122 or be configured to be used by one of the second users 122. For example, the first second-device 120a may be associated with the first second-user 122a, the second second-device 120b may be associated with the second second-user 122b, and the third second-device 120c may be associated with the third second-user 122c.

The second devices 120 may be associated with the second users 122 based on the second devices 120 being configured to be used by the second users 122. For example, the first second-device 120a may have settings or other configuration profiles that are set for the first second-user 122a. In these and other embodiments, the first second-user 122a may be registered with the communication system 130. The registration of the first second-user 122a may include a device that may be used by the first second-user 122a in communication sessions and the first second-device 120a may be listed in the registration of the first second-user 122a. Alternatively or additionally, the first second-device 120a may be associated with the first second-user 122a by the first second-user 122a being the owner of the first second-device 120a and/or being controlled by the first second-user 122a. For example, the first second-device 120a may be controlled by the first second-user 122a when the first second-device 120a is obtaining commands and input from the first second-user 122a or the first second-user 122a is logged into the first second-device 120a such that the first second-device 120a is running a profile or configuration of the first second-user 122a.

During a communication session, audio and/or video may be presented by the second devices 120 for the second users 122. Alternatively or additionally, a transcription of the audio presented by the second devices 120 during a communication session may be presented for the second users 122 during the communication session. In some embodiments, during a communication session with the first device 110, audio and video of the second users 122 may be captured by the second devices 120 and provided to the first device 110.

In some embodiments, information about each of the second users 122 may be associated with one of the second devices 120. For example, information about the first second-user 122a may be associated with the first second-device 120a that is associated with the first second-user 122a. In these and other embodiments, the second devices 120 selected for communication sessions with the first device 110 may be selected based on information about the second users 122. In some embodiments, the second users 122 may be health care professionals. In these and other embodiments, health care professionals may be individuals with training or skills to render advise with respect to mental or physical health, including, nurses, nurse practitioners, medical assistants, doctors, physician assistants, counselors, psychiatrists, psychologists, doulas, among other health care professionals.

In some embodiments, the communication system 130 may include any configuration of hardware, such as processors, servers, and databases that are networked together and configured to perform one or more tasks. For example, the communication system 130 may include multiple computing systems, such as multiple servers that each include memory and at least one processor, which are networked together and configured to perform operations as described in this disclosure, among other operations. In some embodiments, the communication system 130 may include computer-readable-instructions on one or more computer-readable media that are configured to be executed by one or more processors in the communication system 130 to perform operations described in this disclosure. Generally, the communication system 130 may be configured to establish and manage communication sessions between the first device 110 and one or more of the second devices 120. The profile database 132 may be a combination of hardware, including processors, memory, and other hardware configured to store and manage data. In some embodiments, the profile database 132 may be configured to store profile data concerning the first user 112.

An example of the interaction of the elements illustrated in the environment 100 is now provided. As described below, the elements illustrated in the environment 100 may interact to establish a communication session between the first device 110 and one or more of the second devices 120 to allow the first user 112 and at least one of the second users 122 to communicate.

In these and other embodiments, the first user 112 may be an individual in their home who has a health care need. For example, the first user 112 may be an individual at home who is recovering from a surgery and who has a need for in-home care from a health care professional. Alternatively or additionally, the first user 112 may be an individual at home who has an illness for which in-home care from a health care professional is preferable. Alternatively or additionally, the first user 112 may be an individual at a care facility or some other facility. The second users 122 may be health care professionals, one or more of whom may include training to assist the first user 112 with their medical issues.

In some embodiments, before the first device 110 sends a request for a communication session to the communication system 130, the first device 110 may be associated with the first user 112 by the communication system 130. For example, an identifier may be obtained by the communication system 130. The identifier may be specific to the first device 110 and/or first user 112 and may be used by the communication system 130 to indicate the association between the first user 112 and the first device 110. Thus, by the identifier, the communication system 130 may recognize the first device 110 and understand that the first device 110 is associated with the first user 112. In these and other embodiments, the identifier may be provided by the communication system 130 to the first device 110. Thus, when the first device 110 provides the identifier to the communication system 130 with the request for the communication session, the communication system 130 may determine that the first device 110 is associated with the first user 112. Based on the association, the communication system 130 may make determinations based on communication session requests from the first device 110. The identifier may be selected by the communication system 130. For example, based on information regarding the first user 112, the communication system 130 may select the identifier for the first device 110 and/or first user 112.

In some embodiments, before the first device 110 requests the communication system 130 for a communication session, the communication system 130 may obtain profile data regarding the first user 112. In some embodiments, the first device 110 may provide the communication system 130 with the profile data. Alternatively or additionally, another device may provide the profile data of the first user 112 to the communication system 130. In these and other embodiments, the first device 110 may also obtain and store the profile data. Alternatively or additionally, the profile data may not be shared with the first device 110 or a portion of the profile data may be shared with the first device 110. In some embodiments, the communication system 130 may store the profile data in the profile database 132

The profile data may include information about the first user 112, including demographic information, including name, age, sex, address, etc., among other demographic data. The profile data may further include health related information about the first user 112. For example, the health related information may include the height, weight, medical allergies, and current medical conditions, etc., among other health related information. The profile data may further include other information about the first user 112, such as information generated through communication sessions with the second users 122. For example, the profile data may include transcriptions of conversations between the first user 112 and one or more of the second users 122.

After the initialization procedure, the communication system 130 may include information to allow the communication system 130 to recognize that the first device 110 is associated with the first user 112 and the communication system 130 may have obtained the profile data of the first user 112. Furthermore, after the initialization procedure, the first device 110 may send the communication system 130 a request for a communication session. In these and other embodiments, the first user 112 may interact with the first device 110. For example, the first device 110 may obtain input from the first user 112 that may cause the first device 110 to send a communication request to the communication system 130 for a communication session. In some embodiments, the communication request may include the identifier for the first device 110 and/or the first user 112 and/or other information regarding the first user 112.

In some embodiments, the request for the communication session may be sent to a communication address of the communication system 130. For example, the communication address of the communication system 130 may include a uniform resource identifier unique to the communication system 130. In some embodiments, the first device 110 may be provided with the communication address before the request for the communication session is obtained by the first device 110. For example, at power-up, at certain particular intervals, or at other times, the first device 110 may send a request to the communication system 130 for the communication address for communication sessions. For example, the request for the communication address may be sent to a first endpoint of the communication system 130 and the communication address may indicate a second endpoint of the communication system 130. Alternatively or additionally, the first device 110 may obtain the communication address in response to user input to send a request for a communication session. Alternatively or additionally, during the provisioning of the first device 110, the first device 110 may be provided with the communication address.

The first device 110 may send the communication request to the communication address over the first network 102 such that the communication request is received by the communication system 130. The communication address may not identify any of the second devices 120 with which a communication session may be established. Rather, the communication address may simply identify the communication system 130.

In some embodiments, in response to receiving the communication request, the communication system 130 may establish a communication session between the first device 110 and one or more of the second devices 120. In these and other embodiments, the communication system 130 may select one or more of the second devices 120 to participate in the communication session with the first device 110. To select the one or more of the second devices 120, the communication system 130 may use information in the communication request, such as the identifier of the first device 110 and/or the first user 112, to obtain the profile data associated with the first device 110, through the association of the first device 110 and the first user 112, from the profile database 132. Using the profile data, the communication system 130 may select one or more of the second devices 120 for the communication session. For example, using the profile data, the communication system 130 may identify a second user Using the profile data may reduce network usage and communication connections as the communication system 130 may select a device for the communication session that is more adequately suited for the communication session, thereby reducing a number of transfers between devices to select an appropriate device for the communication session. In some embodiments, a device may be more adequately suited for the communication session based on a second user being associated with the device.

In these and other embodiments, the communication system 130 may not request additional information or data from the first device 110 to select among the second devices 120 for the communication session. In these and other embodiments, the communication system 130 may not request additional information or data from the first device 110 based on the communication system 130 using the profile data previously obtained by the communication system 130. In particular, the first device 110 may not obtain additional information or data from the first user 112 that may be used by the communication system 130 to select among the second devices 120 after the first device 110 obtains input from the first user 112 to make the communication request. As a result, in these and other embodiments, a communication session may be established by the communication system 130 through a single user interaction with the first device 110. For example, the communication session may be established by the first user 112 selecting a single icon, saying a single phrase, or otherwise providing a single instruction to the first device 110.

In response to selecting one or more of the second devices 120, the communication system 130 may establish a communication session between the first device 110 and the selected one or more of the second devices 120. In this manner, the first user 112 may communicate with the second users 122 associated with the selected one or more of the second devices 120. In some embodiments, the communication session may include a video communication session that includes video and audio shared between the first device 110 and the selected one or more of the second devices 120. Alternatively or additionally, the communication session may include an audio communication session that includes audio shared between the first device 110 and the selected one or more of the second devices 120.

During a communication session, first device audio from the first device 110 may be provided to the selected one or more of the second devices 120. The selected one or more of the second devices 120 may be configured to present the first device audio. For example, the selected one or more of the second devices 120 may be configured to broadcast the first device audio. Additionally, second device audio from the selected one or more of the second devices 120 may be provided to the first device 110. The first device 110 may be configured to present the second device audio. For example, the first device 110 may be configured to broadcast the second device audio by way of a speaker.

In some embodiments, first transcript data may be generated for the first device audio. The first transcript data may include a transcription of the first device audio. The first transcript data may be provided to the selected one or more of the second devices 120. Alternatively or additionally, second transcript data may be generated for the second device audio. The second transcript data may include a transcription of the second device audio. The second transcript data may be provided to the first device 110.

In some embodiments, one or more of the first transcript data and the second transcript data may be generated in substantially real-time during the communication session. In these and other embodiments, one or more of the first transcript data and the second transcript data may be sent to the selected one or more of the second devices 120 and the first device 110, respectively, in substantially real-time during the communication session. In some embodiments, the communication system 130 may be configured to generate the first and second transcript data and send the first and second transcript data to the first device 110 and the selected one or more of the second devices 120. Alternatively or additionally, another system may generate the first and second transcript data and send the first and second transcript data to the first device 110 and the selected one or more of the second devices 120. Alternatively or additionally, another system may generate the first and second transcript data and the communication system 130 may assist in sending the first and second transcript data to the first device 110 and the selected one or more of the second devices 120.

In some embodiments, the first device 110 may present the transcription of the second device audio. In some embodiments, the first device 110 may present the transcription of the second device audio concurrently with the presentation of the second device audio. In these and other embodiments, the transcription of the second device audio may be presented in substantially real time with the second device audio. For example, a portion of the second device audio may be presented, e.g., broadcast from a speaker on the first device 110. A portion of the transcription of the second device audio that corresponds to the portion of the second device audio may also be displayed on a display of the first device 110 at substantially the same time as the portion of the second device audio is broadcast by the first device 110. For example, the portion of the transcription of the second device audio may be presented within 1, 5, 10, or 15 seconds of the portion of the second device audio being broadcast by the first device 110. By presenting the transcription of the second device audio concurrently with the presentation of the second device audio, the first user 112 may be able to confirm or gain understanding of the second device audio. Furthermore, presenting the transcription of the second device audio may reduce network usage and communication connections as a number of additional communications that may occur due to misunderstanding may be reduced.

In some embodiments, the selected one or more of the second devices 120 may present the transcription of the first device audio. In some embodiments, the selected one or more of the second devices 120 may present the transcription of the first device audio concurrently with the presentation of the first device audio. In these and other embodiments, the transcription of the first device audio may be presented in substantially real time with the first device audio.

In some embodiments, the first transcript data and/or the second transcript data may be stored by the communication system 130. In these and other embodiments, the first transcript data and/or the second transcript data may be part of the profile data of the first user 112 that is associated with the first device 110. As a result, the selection of the second devices 120 for a communication session with the first device 110 may be based on the first transcript data and/or the second transcript data given that the selection may be based on the profile data as indicated above. Thus, past communication sessions between the first device 110 and the second devices 120 may help to inform which of the second devices 120 to select for a future communication session.

Modifications, additions, or omissions may be made to the environment 100 without departing from the scope of the present disclosure. For example, in some embodiments, one or more of the second devices 120 may not be associated with a single one of the second users 122. In these and other embodiments, the one or more of the second devices 120 may be a device configured to select among one or more third devices. In these and other embodiments, the first device 110 may establish a communication session with one or more of the third devices. For example, the first second-device 120a may be a proxy server for the third devices. In these and other embodiments, the communication request from the first device 110 may be provided to the first second-device 120a from the communication system 130. The first second-device 120a may select one or more third devices networked with the first second-device 120a. A communication session between the first device 110 and the selected one or more of the third devices may be established.

In some embodiments, the communication address obtained by the first device 110 may directly indicate one or more of the second devices 120. In these and other embodiments, the communication address may route the communication request through the communication system 130. In these and other embodiments, the one or more of the second devices 120 to which the communication request may be directly routed may be selected based on the profile data of the first user 112. In these and other embodiments, the communication address may be obtained by the first device 110 from the communication system 130 such that the communication system 130 may select the one or more of the second devices 120 before the communication request is sent by the first device 110. In these and other embodiments, the one or more of the second devices 120 may be a proxy server or another device configured to select among one or more third devices with whom the communication session may be established.

Figure 2:
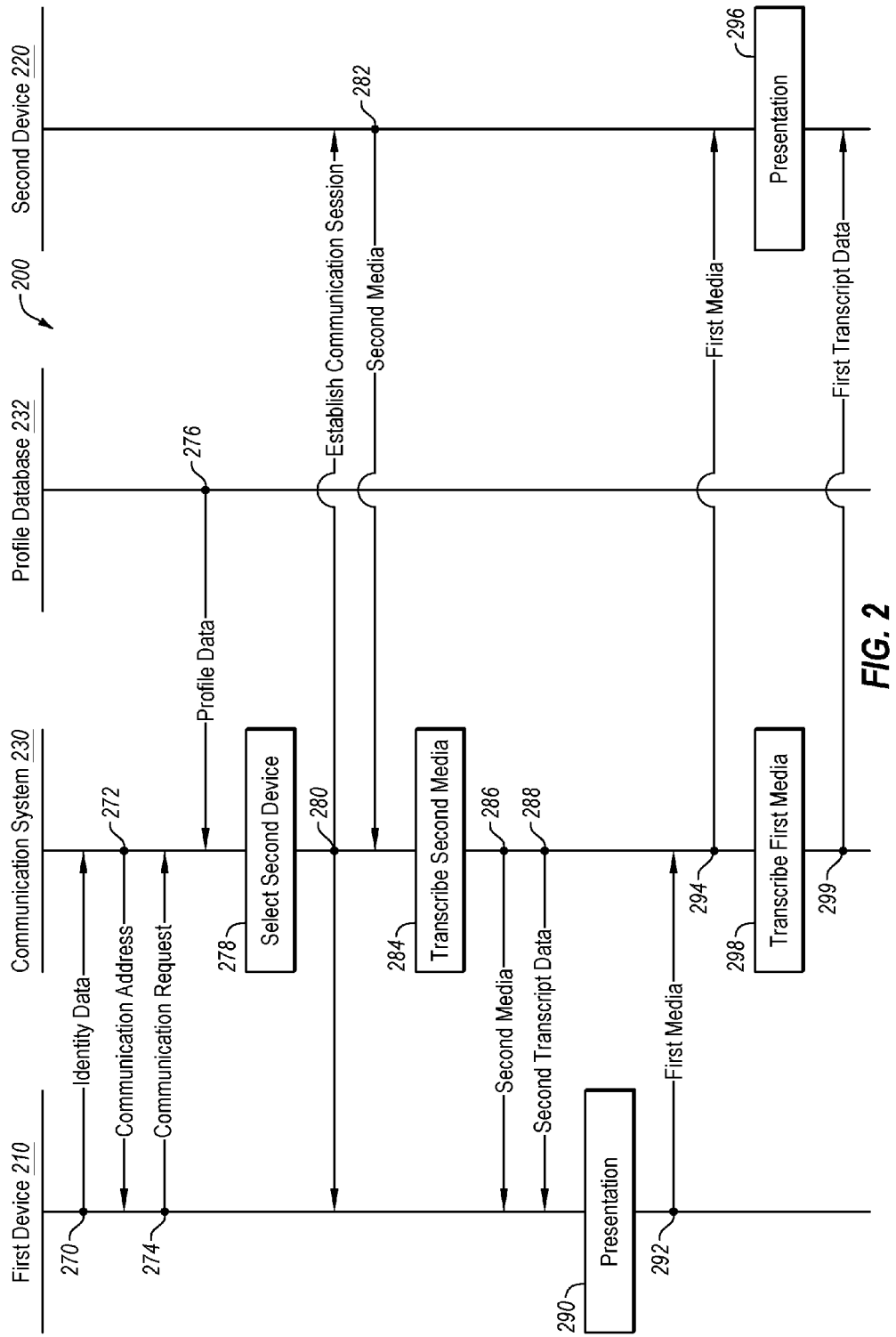
FIG. 2 illustrates example operations in device to device communication.

FIG. 2 illustrates example operations 200 in device to device communication. The operations 200 may be arranged in accordance with at least one embodiment described in the present disclosure. The operations 200 may be between a first device 210, a second device 220, a communication system 230, and a profile database 232. In some embodiments, the first device 210, the second device 220, the communication system 230, and the profile database 232 may be analogous to the first device 110, one of the second devices 120, the communication system 130, and the profile database 132 of FIG. 1. Accordingly, no further explanation is provided with respect thereto.

In some embodiments, the operations 200 may be an example of communications and interactions between the first device 210, the second device 220, the communication system 230, and the profile database 232 that may occur over one or more networks. The operations 200 illustrated are not exhaustive but are merely representative of operations 200 that may occur. Furthermore, one operation as illustrated may represent one or more communications, operations, and/or data exchanges. The operations 200 generally relate to the establishing and maintaining of communication sessions between the first device 210 and the second device 220. In some embodiments, the first device 210 may be associated with and used by a first user, such as a patient. In these and other embodiments, the second device 220 may be associated with and used by a second user, such as a health care professional in a position to render aid to the first user.

At an operation 270, the first device 210 may be configured to provide identity data to the communication system 230 over a network. The identity data may be data associated with the first user who is associated with the first device 210. For example, the identity data may be a name, user identification for the communication system 230, or other information the communication system 230 associates with the user. Alternatively or additionally, the identity data may be an identifier previously provided to the first device 210 from the communication system 230 that associates the first device 210 with the first user.

At operation 272, the communication system 230 may provide the first device 210 with a communication address of the communication system 230. In some embodiments, the operation 272 may be performed in response to the communication system 230 receiving the identify data from the first device 210. In some embodiments, the communication system 230 may select the communication address based on the identity data provided by the first device 210. In some embodiments, the communication address may be a uniform resource identifier (URI). In these and other embodiments, the communication address may specifically address the communication system 230 but may not include an address for the second device 220. Alternatively or additionally, the communication address may include an address for the second device 220 that includes the communication system 230 as a routing intermediary. In some embodiments, the communication address may be configured by the communication system 230 to be unique to the first device 210. In these and other embodiments, when the communication system 230 receives a communication request at the communication address the communication system 230 may identify the communication request as originating at the first device 210 without further information from the first device 210.

At operation 274, the first device 210 may send a communication request to the communication system 230. In some embodiments, the communication request may be sent to the communication address provided to the first device 210 by the communication system 230. In some embodiments, the communication request may follow a communication protocol. For example, the communication request may follow a session initiation protocol (SIP). In these and other embodiments, the first device 210 and the second device 220 may act as user agents and the communication system 230 may act as a proxy server or registrar. In these and other embodiments, the communication request may be a SIP request and the communication address may be a URI that allows a network to route the SIP request to the communication system 230. In these and other embodiments, the SIP request may include a message header field that includes an identifier of the first device 210 that associates the first device 210 with the first user in the communication system 230. In some embodiments, other communication protocols may be used. For example, the protocol may be a H.323, WebRTC, or MDCP protocol among other IP based communication session protocols.

At operation 276, the communication system 230 may obtain profile data from the profile database 232. The profile data obtained may be associated with the first user that is associated with the first device 210. In some embodiments, the communication system 230 may obtain the profile data in response to obtaining the communication request from the first device 210. In these and other embodiments, the communication system 230 may request and obtain the profile data associated with the first user of the first device 210 based on the information from the communication request received from the first device 210. For example, the communication system 230 may use information from the communication request to request the profile data from the profile database 232. The information may include an identifier associated with the first device 210, information from the request based on the communication session protocol, among other information.

At operation 278, the communication system 230 may select a second device for the communication session requested by the first device 210. In some embodiments, the communication system 230 may select the second device 220 using the profile data. For example, the profile data may include information about the first user of the first device 210 that may be used to select a second user of multiple second users that may communicate with the first user. For example, the communication system 230 may include or obtain information about each of the second users. The communication system 230 may use the profile data to establish certain criteria for the second user for the communication session. The communication system 230 may search the information of the multiple second users to identity a particular second user that may satisfy the certain criteria. After identifying the particular second user, the communication system 230 may select a second device associated with the second user. As described in this embodiments, the second device selected by the communication system 230 may be the second device 220.

At operation 280, the communication system 230 may establish a communication session between the first device 210 and the second device 220. In these and other embodiments, the communication system 230 may establish the communication session by sending a request to the second device 220 using the communication session protocols. The request may include information concerning the first device 210. In some embodiments, the communication system 230 may rewrite a portion of the communication request from the first device 210 to send the rewritten communication request to the second device 220. For example, the communication request may be rewritten based on the communication protocol to send a communication request that identifies the first device 210 to the second device 220. Following the communication protocol, such as SIP, the communication session between the first device 210 and the second device 220 that is routed through the communication system 230 may be established.

At operation 282, the second device 220 may capture audio and video of a second user and send the captured audio and video as second media to the communication system 230. In some embodiments, a real-time transport protocol (RTP) or other type of media streaming protocol may be used for transmission of the second media to the communication system 230.

At operation 284, the communication system 230 may generate second transcript data of the second audio received from the second device 220. The second transcript data of the second audio may include a transcription of words included in the second audio. In some embodiments, the second transcript data of the second audio may be made in substantially real-time or concurrently with reception of the second audio. In these and other embodiments, the second transcript data may be stored by the communication system 230.

In some embodiments, the second transcript data may be generated by a transcription system that is part of the communication system 230. In some embodiments, the second transcript data may include a machine generated transcription of the second audio. In these and other embodiments, the second audio may be re-voiced by another person before a machine transcription is generated. In these and other embodiments, the other person may make corrections to the machine transcription. Alternatively or additionally, the second transcript data may be generated by a transcription system that is not a part of the communication system 230.

At operation 286, the communication system 230 may provide the second media to the first device 210. At operation 288, the communication system 230 may provide the second transcript data to the first device 210.

At operation 290, the first device 210 may be configured to present the second media and to concurrently present the second transcript data. In these and other embodiments, the first device 210 may present the second transcript data and the video of the second media on a display of the first device 210. The first device 210 may also present the audio of the second media by broadcasting the audio through a speaker of the first device 210. In these and other embodiments, the second transcript data may be presented in substantial real-time with the audio of the second media such that a transcription of the audio of the second media is substantially synchronized with the audio of the second media as it is presented by the first device 210. Substantially synchronized may indicate that there is a delay of less than 1, 2, 5, 10, or 15 seconds between the transcription of the audio and the audio.

At operation 292, the first device 210 may capture audio and video of the first user and send the captured audio and video as first media to the communication system 230. In some embodiments, a RTP or other type of media streaming protocol may be used for transmission of the first media to the communication system 230.

At operation 294, the communication system 230 may provide the first media to the second device 220. At operation 296, the second device 220 may be configured to present the first media. In these and other embodiments, the second device 220 may present the video of the first media on a display of the second device 220 and may present the audio of the first media by a speaker of the second device 220.

At operation 298, the communication system 230 may generate first transcript data of the first audio received from the second device 220. The first transcript data of the first audio may include a transcription of words included in the first audio. In some embodiments, the first transcript data of the first audio may not be made in substantially real-time. For example, the first audio data may be stored in the communication system 230 and the transcription of the first audio data may be made later in the communication session or after the communication session has ended. In some embodiments, the first transcript data may be generated in a similar manner as the second transcript data.

At operation 299, the first transcript data may be sent by the communication system 230 to the second device 220. In these and other embodiments, the first transcript data may be stored by the communication system 230 and/or the second device 220.

Modifications, additions, or omissions may be made to the operations 200 without departing from the scope of the present disclosure. For example, in some embodiments, the operations 200 may not include one or more of the operations. For example, the operations 200 may not include the operations 276 and 278. In these and other embodiments, the communication request provided by the first device 210 may indicate the second device 220 for the communication session. In these and other embodiments, the communication system 230 may establish the communication session between the first device 210 and the second device 220.

In some embodiments, the operations 200 may include additional operations. For example, the communication system 230 may select multiple second devices. In these and other embodiments, the communication system 230 may establish a communication session that includes the first device 210, the second device 220, and other second devices. As another example, in some embodiments, the operations 200 may be arranged in a different order. For example, the operation 286 may occur before the operation 284.

Figure 3:
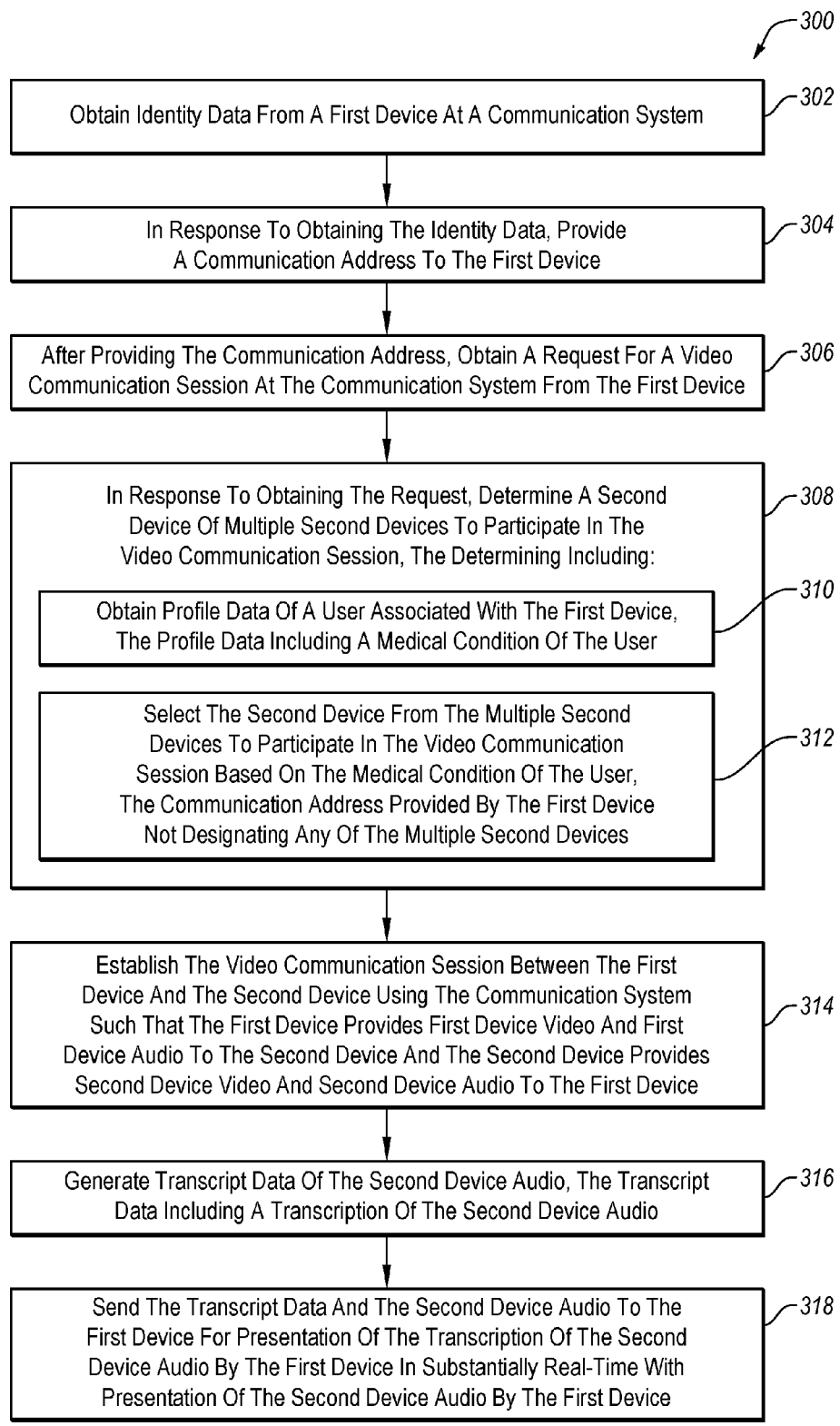
FIG. 3 is a flowchart of an example method of device to device communication.

FIG. 3 is a flowchart of an example method 300 of device to device communication. The method 300 may be arranged in accordance with at least one embodiment described in the present disclosure. The method 300 may be performed, in whole or in part, in some embodiments by a system or combinations of components in a system or environment as described in the present disclosure. For example, the method 300 may be performed, in whole or in part, by the communication system 130, a communication system 530, a communication system 1130, and/or a system 1700 of FIGS. 1, 5, 11, and 17, respectively. In these and other embodiments, some or all of the operations of the method 300 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 300 may begin at block 302, where identity data may be obtained from a first device at a communication system. In block 304, in response to obtaining the identity data, a communication address may be provided to the first device.

In block 306, after providing the communication address, a request for a video communication session may be obtained at the communication system from the first device.

In block 308, in response to obtaining the request, a second device of multiple second devices may be determined to participate in the video communication session. In some embodiments, determining the second device to participate in the video communication session may be performed without receiving additional data from the first device after obtaining the request for the video communication session. In some embodiments, determining the second device to participate in the video communication session may include the block 310 and the block 312.

In block 310, profile data of a user associated with the first device may be obtained. The profile data may include a medical condition of the user. In some embodiments, the communication system may obtain the profile data before the first device sends the request for the video communication session.

In block 312, the second device may be selected from the multiple second devices to participate in the video communication session based on the medical condition of the user. In these and other embodiments, the communication address provided by the first device may not designate any of the multiple second devices or the second device. As a result, the second device may be selected based on the medical condition of the user and not using information from the communication address or request provided by first device. In these and other embodiments, the second device may be used by a health care professional that may be selected based on the profile data.

In block 314, the video communication session may be established between the first device and the second device using the communication system such that the first device provides first device video and first device audio to the second device and the second device provides second device video and second device audio to the first device.

In block 316, transcript data of the second device audio may be generated. The transcript data may include a transcription of the second device audio.

In block 318, the transcript data and the second device audio may be sent to the first device for presentation of the transcription of the second device audio by the first device in substantially real-time with presentation of the second device audio by the first device.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 300 may further include generating second transcript data of the first device audio. In these and other embodiments, the second transcript data may include a transcription of the first device audio. In these and other embodiments, the method 300 may further include associating the second transcript data and the first transcript data with a user of the first device and storing the second transcript data and the first transcript data outside of the first device.

In some embodiments, the method 300 may further include after selecting the second device, providing the medical condition of the user to the second device. In some embodiments, the method 300 may further include obtaining health data of the user using the request for the video communication session and providing the health data of the user and the profile data to the second device for concurrent use with the video communication session.

Figure 4:
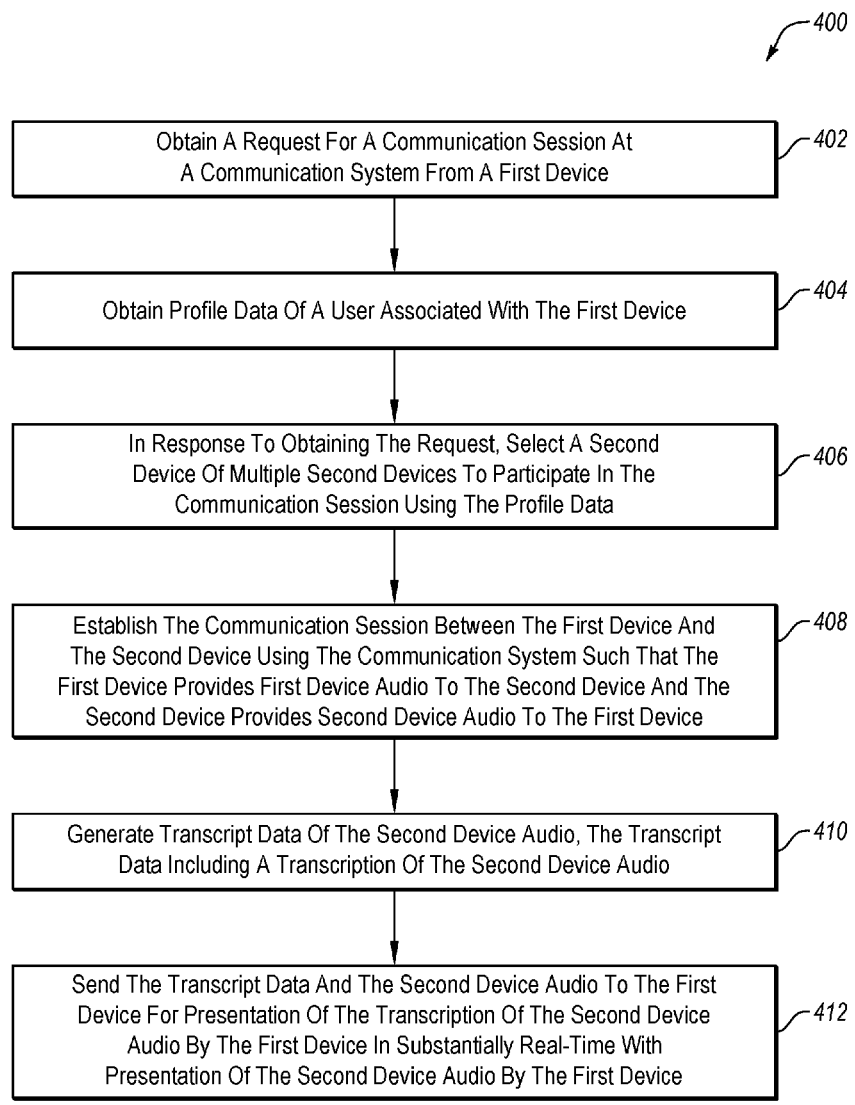
FIG. 4 is a flowchart of another example method of device to device communication.

FIG. 4 is a flowchart of another example method 400 of device to device communication. The method 400 may be arranged in accordance with at least one embodiment described in the present disclosure. The method 400 may be performed, in whole or in part, in some embodiments by a system or combinations of components in a system or environment as described in the present disclosure. For example, the method 400 may be performed, in whole or in part, by the communication system 130, the communication system 530, the communication system 1130, and/or the system 1700 of FIGS. 1, 5, 11, and 17, respectively. In these and other embodiments, some or all of the operations of the method 400 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 400 may begin at block 402, where a request for a communication session may be obtained at a communication system from a first device.

In block 404, profile data of a user associated with the first device may be obtained. In some embodiments, the communication system may obtain the profile data before the communication system obtains the request for the communication session.

In block 406, in response to obtaining the request, a second device of multiple second devices may be selected to participate in the communication session using the profile data. In some embodiments, selecting the second device may be performed without receiving additional data from the first device after obtaining the request for the communication session.

In block 408, the communication session between the first device and the second device may be established using the communication system such that the first device provides first device audio to the second device and the second device provides second device audio to the first device.

In block 410, transcript data of the second device audio may be generated. The transcript data may include a transcription of the second device audio.

In block 412, the transcript data and the second device audio may be sent to the first device for presentation of the transcription of the second device audio by the first device in substantially real-time with presentation of the second device audio by the first device.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 400 may further include generating second transcript data of the first device audio, the second transcript data including a transcription of the first device audio. As another example, the method 400 may further include associating the second transcript data and the first transcript data with a user of the first device and storing the second transcript data and the first transcript data outside of the first device.

Figure 5:
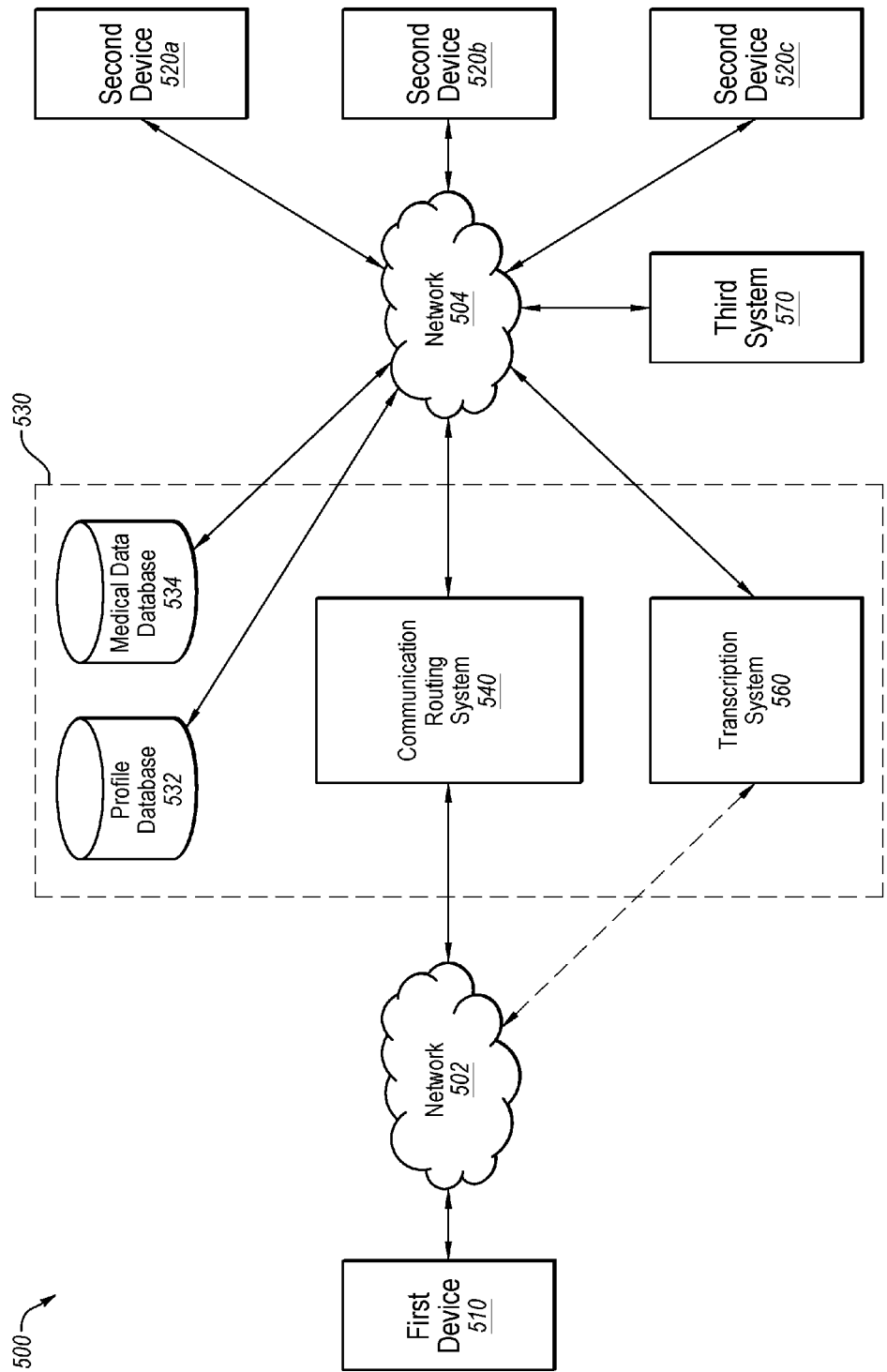
FIG. 5 illustrates another example environment related to device to device communication.

FIG. 5 illustrates another example environment 500 related to device to device communication. The environment 500 may be arranged in accordance with at least one embodiment described in the present disclosure. The environment 500 may include a first network 502; a second network 504; a first device 510; second devices 520, including a first second-device 520a, a second second-device 520b, and a third second-device 520c; a communication system 530 that includes a profile database 532, a medical data database 534, a communication routing system 540, and a transcription system 560; and a third system 570.

The first network 502, the second network 504, the first device 510, and the second devices 520, in some respects may be analogous to the first network 102, the second network 104, the first device 110, and the second devices 120 of FIG. 1. Accordingly, limited or no further explanation may be provided with respect to certain aspects of one or more of these elements in the discussion of FIG. 5.

In some embodiments, each of the communication routing system 540, the transcription system 560, and the third system 570 may include any configuration of hardware, such as processors, servers, and databases that are networked together and configured to perform one or more tasks. For example, each of the communication routing system 540, the transcription system 560, and the third system 570 may include multiple computing systems, such as multiple servers that each include memory and at least one processor, which are networked together and configured to perform operations as described in this disclosure, among other operations. In some embodiments, each of the communication routing system 540, the transcription system 560, and the third system 570 may include computer-readable-instructions on one or more computer-readable media that are configured to be executed by one or more processors in each of the communication routing system 540, the transcription system 560, and the third system 570 to perform operations described in this disclosure.

Generally, the communication routing system 540 may be configured to establish and manage communication sessions between the first device 510 and one or more of the second devices 520 and/or the third system 570. The transcription system 560 may be configured to generate and provide transcriptions of audio from communication sessions established by the communication routing system 540.

The profile database 532 and the medical data database 534 may be a combination of hardware, including processors, memory, and other hardware configured to store and manage data. In some embodiments, the profile database 532 may be configured to store profile data concerning a first user associated with the first device 510. In these and other embodiments, the profile data may be analogous to the profile data described with respect to FIG. 1.

In some embodiments, the medical data database 534 may be configured to store medical data concerning the first user associated with the first device 510. In these and other embodiments, the medical data may include electronic health records of the first user. Alternatively or additionally, the medical data may include other data regarding previous and current health conditions of the first user, including previous and current diseases, treatments, family history, and medical history.

An example of the interaction of the elements illustrated in the environment 500 is now provided. As described below, the elements illustrated in the environment 500 may interact to establish a communication session between the first device 510 and one or more of the second devices 520 and the third system 570 and to transcribe the communication session.

The first device 510 may send a request for a communication session to the communication routing system 540. The communication routing system 540 may obtain the request from the first device 510. Based on the request, the communication routing system 540 may access the profile database 532 to obtain profile data regarding the first user associated with the first device 510. Using the profile data, the communication routing system 540 may select the third system 570 and one or more of the second devices 520 for the communication session with the first device 510. After selecting one or more of the second devices 520 and the third system 570, the communication routing system 540 may establish the communication session.

In some embodiments, the communication routing system 540 may also be configured to provide the profile data of the first user to the selected one or more of the second devices 520 and the third system 570. Alternatively or additionally, the communication routing system 540 may be configured to obtain medical data of the first user from the medical data database 534 based on the communication request. In these and other embodiments, the communication routing system 540 may use the medical data to select the one or more of the second devices 520 and the third system 570. Alternatively or additionally, the communication routing system 540 may provide the medical data to the selected one or more of the second devices 520 and the third system 570. The selected one or more of the second devices 520 and the third system 570 may present the profile data and/or the medical data to second users of the selected one or more of the second devices 520 and the third system 570. The second users of the one or more of the second devices 520 and the third system 570 may use the medical data and/or the profile data to assist the first user during the communication session.

In some embodiments, the communication routing system 540 may provide a limited amount of the profile data and the medical data database 534 to some of the selected one or more of the second devices 520 and the third system 570 while others of the selected one or more of the second devices 520 and the third system 570 may obtain full access. In these and other embodiments, the communication routing system 540 may determine an amount of access to the profile data and the medical data based on the second users of the selected one or more of the second devices 520 and the third system 570. For example, a second user of a selected second device 520 may be a health professional that may obtain full access to the profile data and the medical data. A user of the third system 570 may be a relative of the first user or other non-health professional in the communication session. In these and other embodiments, the user of the third system 570 may obtain limited access to the profile data and the medical data.

In some embodiments, the communication routing system 540 may be configured to join another of the second devices 520 and/or the third system 570 during a communication session of the first device 510 and one of the second devices 520 or the third system 570. For example, during a communication session between the first device 510 and the first second-device 520a, the first second-device 520a may provide a request to join the third system 570 to the communication session. The communication routing system 540 may then establish communications with the third system 570 and join the third system 570 to the communication session between the first device 510 and the first second-device 520a. For example, a second user of the first second-device 520a may be a nurse and a third user of the third system 570 may be a medical doctor. During the communication session, the nurse may request that the medical doctor join the communication session to provide further assistance to the first user of the first device 510.

During a communication session the first device 510 and a selected one or more of the second devices 520 and the third system 570, the communication routing system 540 may be configured to receive media data from the first device 510 and the selected one or more of the second devices 520 and the third system 570. The communication routing system 540 may route the media data to the transcription system 560 for generation of transcript data. The communication routing system 540 may also route the transcript data from the transcription system 560 to the first device 510 and the selected one or more of the second devices 520 and the third system 570. Further explanation of the transcription process and routing is now described. However, it is described in the context of a communication session between the first device 510 and the first second-device 520a for ease of explanation.

As mentioned, the first device 510 and the first second-device 520a may exchange media data during a communication session. In some embodiments, the media data may include video and audio data. For example, the first device 510 may send first audio data and first video data to the first second-device 520a and the first second-device 520a may send second audio data and second video data to the first device 510. Alternatively or additionally, the media data may include audio data but not video data. For example, the first device 510 may receive audio and video data from the first second-device 520a but the first second-device 520a may receive audio data but not video data from the first device 510.

During the communication session, the media data exchanged between the first device 510 and the first second-device 520a may be routed through the communication routing system 540. During the routing of the media data between the first device 510 and the first second-device 520a, the communication routing system 540 may be configured to duplicate the audio from the media data and provide the duplicated audio to the transcription system 560.

For example, the communication routing system 540 may obtain the first audio and the first video from the first device 510. In some embodiments, the first audio and the first video may be separate streams from the first device 510. In these and other embodiments, the communication routing system 540 may duplicate the first audio to generate duplicated first audio. The communication routing system 540 may route the first audio and the first video to the first second-device 520a. Alternatively or additionally, the first audio and the first video may be a merged data stream. In these and other embodiments, the communication routing system 540 may separate the first audio from the first video, generate the duplicated first audio, and route the combined media stream to the first second-device 520a.

The communication routing system 540 may be configured to route the duplicated first audio to the transcription system 560. Before routing the duplicated first audio, the communication routing system 540 may establish a communication link with the transcription system 560 for routing the duplicated first audio to the transcription system 560 and receiving first transcript data of the duplicated first audio from the transcription system 560. Alternatively or additionally, the communication routing system 540 may establish a communication link to route duplicated first audio to the transcription system 560 but not receive the first transcript data from the transcription system 560. In these and other embodiments, the communication routing system 540 may also provide an address of the first second-device 520a to the transcription system 560. In these and other embodiments, the transcription system 560 may establish a communication link with the first second-device 520a for sending the first transcript data of the duplicated first audio to the first second-device 520a.

The transcription system 560 may receive the duplicated first audio. The transcription system 560 may generate the first transcript data of the duplicated first audio. The first transcript data may include a transcription of the duplicated first audio. In some embodiments, the first transcript data may include multiple data segments. Each of the data segments may include a transcription of a portion of the duplicated first audio. For example, the communication session may last for ten minutes. Thus, the transcription system 560 may receive ten minutes of duplicated first audio. In these and other embodiments, each of the data segments of the first transcript data may include a portion of the ten minutes. For example, each of the data segments may include transcriptions of 3, 5, 10, 15, 20, 40, 60, or more seconds of the duplicated first audio. A combination of the data segments may result in a transcription of the duplicated first audio.

Alternatively or additionally, each of the data segments may include a portion of the total transcription of the ten minutes of the duplicated first audio. For example, the data segments may include one or more words, such as 1, 3, 5, 10, 15, 20, or more words in a data segment. In these and other embodiments, a number of words in each data segment may vary.

In some embodiments, the data segments may further include additional information. For example, the data segments may each include an identifier that associates that data segment with a particular communication session. Alternatively or additionally, the data segments may include information about the source device and/or the destination device, e.g., the first device 510, the second device 520, etc. Alternatively or additionally, the data segments may include a time stamp for the communication session or a time stamp associated with the transcription system 560.

In some embodiments, the transcription system 560 may generate the data segments using a machine transcription of the duplicated first audio. In some embodiments, before a machine transcription is made of the duplicated first audio, the duplicated first audio may be listened to and re-voiced by another person. In these and other embodiments, the other person may make corrections to the machine transcription.

The transcription system 560 may provide the first transcript data to the communication routing system 540. The communication routing system 540 may route the first transcript data to the first second-device 520a. The first second-device 520a may present the first transcript data to a user of the first second-device 520a on a display of the first second-device 520a.

The communication routing system 540 and the transcription system 560 may handle the second media data from the first second-device 520a in an analogous manner. For example, the communication routing system 540 may generate duplicated second audio of second audio of the second media data and the transcription system 560 may generate second transcript data based on the duplicated second audio. The second transcript data may be provided to the first device 510 for presentation of the first user of the first device 510.

In some embodiments, the generation and delivery of the transcript data of the first and second media may both be in substantially real-time or real-time. In these and other embodiments, the first device 510 may present the second transcript data concurrently with the second media data in substantially real-time or real-time. Concurrent presentation of the second transcript data and the second media data in substantially real-time may indicate that when audio is presented, a transcription that corresponds to the presented audio is also presented with a delay of less than 1, 2, 5, 10, or 15 seconds between the transcription and the audio.

In some embodiments, the generation and delivery of transcript data of one of the first and second media may be in substantially real-time or real-time and the generation and/or delivery of transcript data of another of the first and second media may not be in real time. For example, the second transcript data provided to the first device 510 may be generated and delivered in substantially real-time but the first transcript data provided to the first second-device 520a may be generated and delivered but not in real-time. For example, the first transcript data may be generated later or after the termination of the communication session.

In some embodiments, the first and the second transcript data may be generated in real-time, but not delivered in real-time. Alternatively or additionally, one of the first and the second transcript data may be generated in real-time, but not delivered in real-time or not delivered at all.

In some embodiments, the duplicated second audio and the duplicated first audio may be provided to the transcription system 560 in a single media stream. In these and other embodiments, the transcription system 560 may associate the duplicated second audio and the duplicated first audio based on the duplicated second audio and the duplicated first audio being generated from audio in a communication session. Alternatively or additionally, each of the duplicated second audio and the duplicated first audio may be provided to the transcription system 560 in a separate media stream. In these and other embodiments, the first transcript data and the second transcript data may be provided to the communication routing system 540 in separate media streams.

In some embodiments, the first transcript data and the second transcript data may be saved by one or more of the transcription system 560, the communication routing system 540, the first device 510, and the first second-device 520a. In some embodiments, one or more of the components that obtains the first transcript data and the second transcript data may provide the first transcript data and the second transcript data to the profile database 532 and/or the medical data database 534. In these and other embodiments, the communication routing system 540 may use the first transcript data and/or the second transcript data to select second devices in response to future communication requests from the first device 510. In some embodiments, the first transcript data and the second transcript data of a first communication session may also be provided to the second devices 520 and/or the third system 570 during subsequent communication sessions with the first device 510.

In some embodiments, one or more of the components of the environment 500 may combine the first transcript data and the second transcript data to generate third transcript data. The third transcript data may include a transcription of the entire communication session. In contrast, the first transcript data may include a transcription of the audio generated by the first device 510 and the second transcript data may include a transcription of the audio generated by the first second-device 520a. In these and other embodiments, the third transcript data may be saved in one or more components of the environment 500.

In some embodiments, the first transcript data and the second transcript data may be combined by interweaving the data segments of the first transcript data and the second transcript data. In these and other embodiments, the data segments of the first transcript data and the second transcript data may be interweaved such that the data segments of the first transcript data and the second transcript data are combined in substantially chronological order.

In some embodiments, when a third device, such as the third system 570 participates in a communication session between the first device 510 and the first second-device 520a, third transcript data may be generated for third audio generated by the third device. In these and other embodiments, the third transcript data may be provided to both the first device 510 and the first second-device 520a and the third device may receive the first and second transcript data from the first device 510 and the first second-device 520a, respectively. Alternatively or additionally, the third transcript data may be provided to one of the first device 510 and the first second-device 520a, such as the first device 510. In these and other embodiments, the third device may not receive the first transcript data or the second transcript data. Alternatively or additionally, the third transcript data may or may not be generated in real-time or substantially real-time. Alternatively or additionally, the third transcript data may or may not be combined with the first transcript data and the second transcript data.

Modifications, additions, or omissions may be made to the environment 500 without departing from the scope of the present disclosure. For example, in some embodiments, the transcription system 560 may be part of the communication routing system 540. Alternatively or additionally, the transcription system 560 may be separate from the communication system 530. In some embodiments, the communication system 530 may include other networks besides the first network 502 and the second network 504 that may allow for communication between the components in the communication system 530.

As another example, in some embodiments, the transcription system 560 may receive the first audio from the first device 510 and the second audio from the second device 520. For example, the first device 510 may send the first audio to the communication routing system 540 for sending to the first second-device 520a and send the first audio to the transcription system 560 to generate the first transcript data, which may be sent to the first second-device 520a. Analogous operations may occur with the second audio and the first second-device 520a.

Alternatively or additionally, the first device 510 may be configured to receive the second audio and provide the second audio to the transcription system 560. In these and other embodiments, the transcription system 560 may generate the second transcript data based on the second audio and provide the second transcript data to the first device 510. Analogous operations may occur with the first audio and the first second-device 520a. In these and other embodiments, the communication routing system 540 may route audio and transcript data between the transcription system 560 and the first device 510 and the second device 520.

Figure 6:
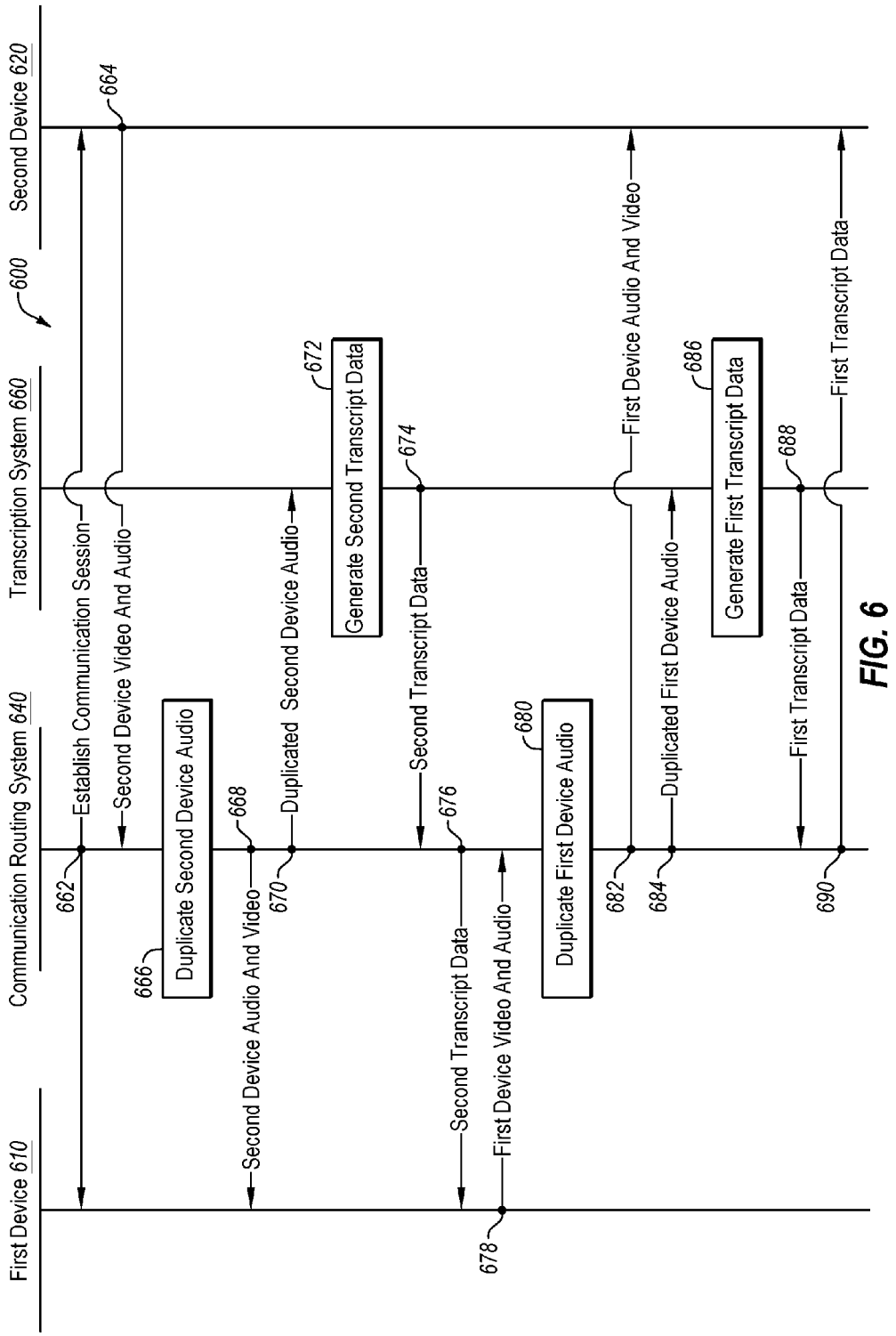
FIG. 6 illustrates example operations in transcription of a communication session between devices.

FIG. 6 illustrates example operations 600 in transcription of a communication session between devices. The operations 600 may be arranged in accordance with at least one embodiment described in the present disclosure. The operations 600 may be between a first device 610, a second device 620, a communication routing system 640, and a transcription system 660. In some embodiments, the first device 610, the second device 620, the communication routing system 640, and the transcription system 660 may be analogous to the first device 510, one of the second devices 520, the communication routing system 540, and the transcription system 560 of FIG. 5. Accordingly, no further explanation is provided with respect thereto.

In some embodiments, the operations 600 may be an example of communications and interactions between the first device 610, the second device 620, the communication routing system 640, and the transcription system 660 that may occur over one or more networks. The operations 600 illustrated are not exhaustive but are merely representative of operations 600 that may occur. Furthermore, one operation as illustrated may represent one or more communications, operations, and/or data exchanges. The operations 600 generally relate to generation of transcript data of a communication session between the first device 610 and the second device 620.

At an operation 662, the communication routing system 640 may establish a communication session between the first device 610 and the second device 620. After establishing the communication session, at operation 664, the second device 620 may send second device audio and second device video to the communication routing system 640. The second device 620 may generate the second device video by capturing images of a user of the second device 620 using a camera on the second device 620. The second device 620 may generate the second device audio by capturing sound generated by the user of the second device 620 using a microphone on the second device 620. The second device video and the second device audio may be digital signals sent to the communication routing system 640 using a media transmission protocol.

At operation 666, the communication routing system 640 may duplicate the second device audio to generate duplicated second device audio. In these and other embodiments, the communication routing system 640 may make a digital copy of the second device audio such that the digital copy of the second device audio may be used as the duplicated second device audio.

At operation 668, the communication routing system 640 may send the second device audio and the second device video to the first device 610. The first device 610 may be configured to present the second device audio and the second device video.

At operation 670, the communication routing system 640 may send the duplicated second device audio to the transcription system 660. At operation 672, the transcription system 660 may generate second transcript data using the duplicated second device audio. The second transcript data may include a transcription of the second device audio.

At operation 674, the transcription system 660 may send the second transcript data to the communication routing system 640. At operation 676, the communication routing system 640 may send the second transcript data to the first device 610. The first device 610 may present a transcription of the second device audio concurrent with the presentation of the second device audio.

In some embodiments, the operations 670, 672, 674, and 676, may occur in real-time such that the first device 610 may be configured to present a transcription of the second device audio concurrent with the presentation of the second device audio in substantially real-time. Furthermore, in some embodiments, the operations 664, 666, 668, 670, 672, 674, and 676, may occur simultaneously and on an ongoing basis as second device audio and video are streamed from the second device 620 through the communication routing system 640 to the first device 610 during a communication session.

Alternatively or additionally, the operations 670, 672, 674, and 676 may occur when it is detected by the communication routing system 640 that there is a voice signal or other signal in second device audio provided to the communication routing system 640. For example, in some embodiments, a user of the second device 620 may not be speaking, such as when the user is listening to the first audio from the first device 610. In these and other embodiments, the communication routing system 640 may detect that there is not a voice signal in the second audio data being received from the second device 620. For example, the communication routing system 640 may detect the voice signal based on an envelope of a magnitude of the second audio data. When the envelope is substantially flat over a particular period, the communication routing system 640 may determine that there is no voice signal. When the envelope varies over the particular period, the communication routing system 640 may determine that there is a voice signal. The particular period may be selected based on average talking speeds and voice inflections for an adult in the language being transcribed. When a voice signal is detected, the operations 670, 672, 674, and 676 may occur. When a voice signal is not detected, the operations 670, 672, 674, and 676 may not occur.

At operation 678, the first device 610 may send first device audio and first device video to the communication routing system 640. The first device 610 may generate the first device video by capturing images of a user of the first device 610 using a camera on the first device 610. The first device 610 may generate the first device audio by capturing sound generated by the user of the first device 610 using a microphone on the first device 610. The first device video and the first device audio may be digital signals sent to the communication routing system 640 using a media transmission protocol.

At operation 680, the communication routing system 640 may duplicate the first device audio to generate duplicated first device audio. In these and other embodiments, the communication routing system 640 may make a digital copy of the first device audio such that the digital copy of the first device audio may be used as the duplicated first device audio.

At operation 682, the communication routing system 640 may send the first device audio and the first device video to the second device 620. The second device 620 may be configured to present the first device audio and the first device video.

At operation 684, the communication routing system 640 may send the duplicated first device audio to the transcription system 660. At operation 686, the transcription system 660 may generate the first transcript data using the duplicated first device audio. The first transcript data may include a transcription of the first device audio.

At operation 688, the transcription system 660 may send the first transcript data to the communication routing system 640. At operation 690, the communication routing system 640 may send the first transcript data to the second device 620.

In some embodiments, the operations 684, 686, 688, and 690, may occur in real-time such that the second device 620 may be configured to present a transcription of the first device audio concurrent with the presentation of the first device audio in substantially real-time. Alternatively or additionally, one or more of the operations 684, 686, 688, and 690 may not occur in real-time. For example, the duplicated first device audio may be stored by the communication routing system 640 for a time period before being sent to the transcription system 660. Alternatively or additionally, the transcription system 660 may store the duplicated first device audio before generating the first transcript data. Alternatively or additionally, the transcription system 660 may generate the first transcript data, but may not send the first transcript data to the communication routing system 640 or the communication routing system 640 may not send the first transcript data to the second device 620. In these and other embodiments, one or more of the operations 684, 686, 688, and 690 may occur after the communication session ends or later in the communication session. Alternatively or additionally, the operations 684, 686, 688, and 690 may occur when it is detected by the communication routing system 640 that there is a voice signal or other sound signal in the first device audio provided to the communication routing system 640.

In some embodiments, the operations 664, 680, and 682 may occur simultaneously and on an ongoing basis as first device audio and video are streamed from the first device 610 through the communication routing system 640 to the second device 620 during the communication session.

Modifications, additions, or omissions may be made to the operations 600 without departing from the scope of the present disclosure. For example, in some embodiments, the operations 600 may not include one or more of the operations. For example, the operations 600 may not include the operation 690 as the first transcript data may not be provided to the second device 620. In some embodiments, the operations 600 may include additional operations. For example, the communication routing system 640 may be configured to store the second transcript data and the first transcript data or configured to provide the second transcript data and the first transcript data to a database for storage. In these and other embodiments, the communication routing system 640 may combine the second transcript data and the first transcript data.

Figure 7:
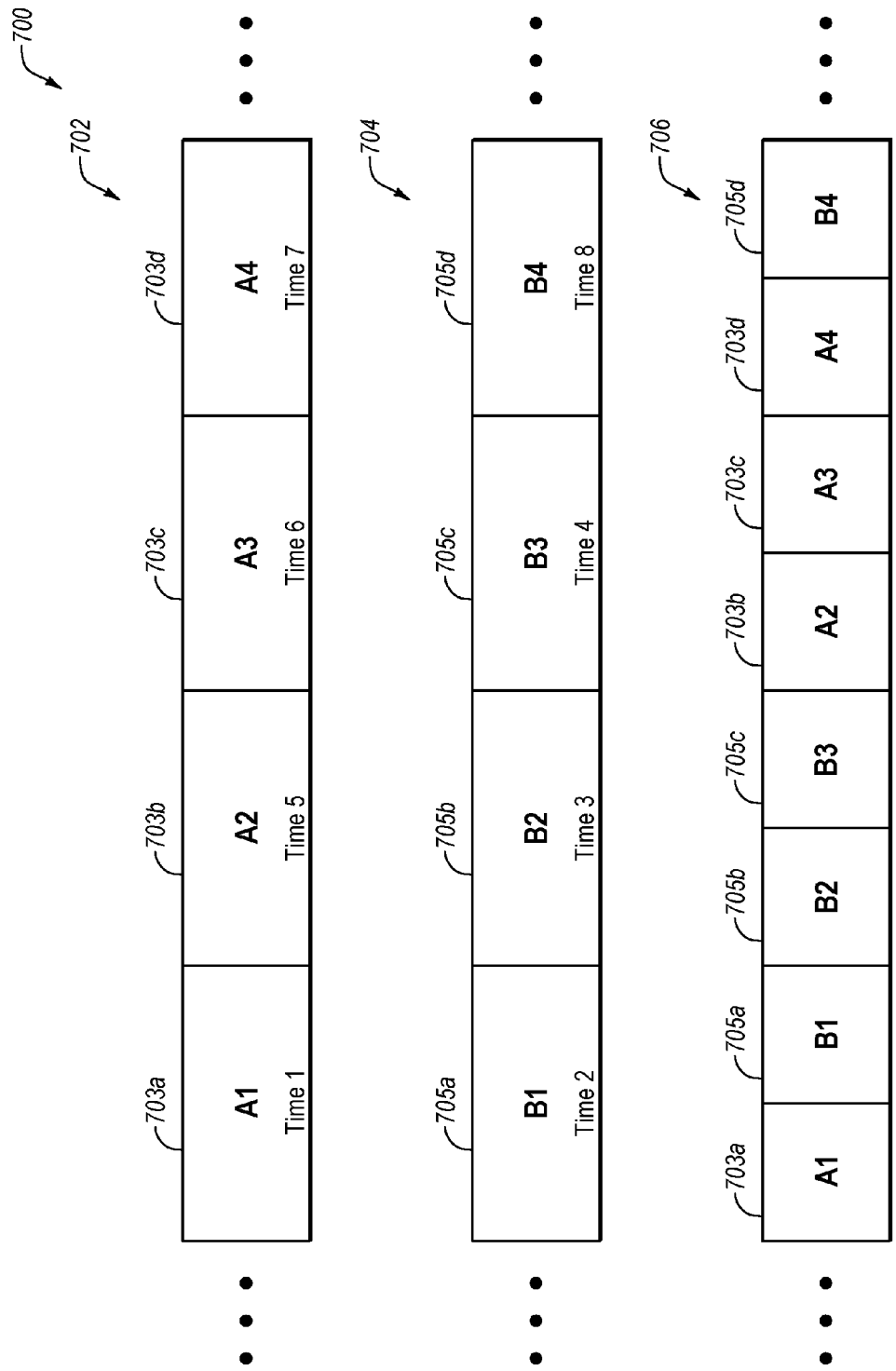
FIG. 7 illustrates an example diagram of combining transcript data.

FIG. 7 illustrates an example diagram 700 of combining transcript data. The diagram 700 may be arranged in accordance with at least one embodiment described in the present disclosure. The diagram 700 illustrates first transcript data 702, second transcript data 704, and third transcript data 706. In particular, the diagram 700 illustrates an example combination of the first transcript data 702 with the second transcript data 704 to create the third transcript data 706.

The first transcript data 702 includes first data segments 703, including first first-data segment 703a, second first-data segment 703b, third first-data segment 703c, and fourth first-data segment 703d. Each of the first data segments 703 includes one or more words, represented by A1, A2, A3, and A4. The second transcript data 704 includes second data segments 705, including first second-data segment 705a, second second-data segment 705b, third second-data segment 705c, and fourth second-data segment 705d. Each of the second data segments 705 includes one or more words, represented by B1, B2, B3, and B4.

Each of the first data segments 703 and the second data segments 705 further include a time. The times are represented as Time 1 through Time 8. The numbering of the times as Time 1 through Time 8 represent arbitrary times, but the numbering of 1-8 illustrates a chronological order from Time 1 to Time 8.

As illustrated in diagram 700, the first transcript data 702 and the second transcript data 704 are combined by determining a data segment of the first data segments 703 and the second data segments 705 that has the earliest time. The data segment with the earliest time is used to start the third transcript data 706. The data segment of the first data segments 703 and the second data segments 705 with the next time is then added to the third transcript data 706. Remaining data segments are added in chronological order as illustrated.

In some embodiments, one or more of the data segments from the first data segments 703 and the second data segments 705 may have a substantially similar or similar time. In these and other embodiments, an ordering of the data segments may be selected based on the words and/or punctuation in the data segments and adjacent data segments of the data segments in question. For example, if the second first-data segment 703b and the second second-data segment 705b have substantially similar or similar times, the wording and or punctuation of the second first-data segment 703b and/or the second second-data segment 705b and their adjacent data segments may be reviewed. If either of the second first-data segment 703b or the second second-data segment 705b included punctuation, then the data segment with the punctuation may be placed ahead of the other data segment in the third transcript data 706. As another example, punctuation of the data segments surrounding the data segments in question may be analyzed to determine an ordering of the data segments.

Modifications, additions, or omissions may be made to the diagram 700 and/or the described method of combining transcript data without departing from the scope of the present disclosure.

Figure 8A:
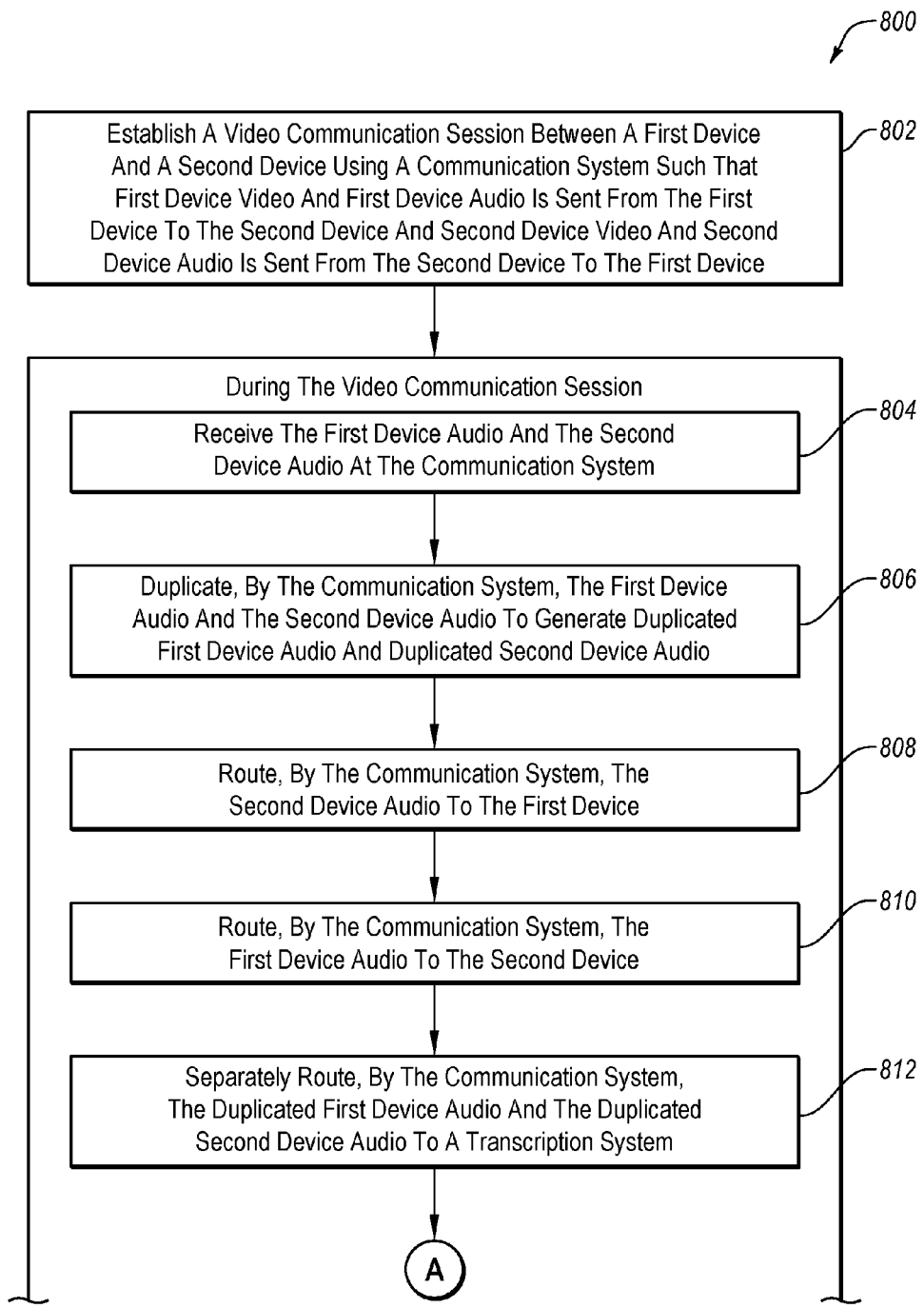
FIGS. 8a and 8b illustrate a flowchart of an example method to transcribe communication sessions between devices.
Figure 8B:
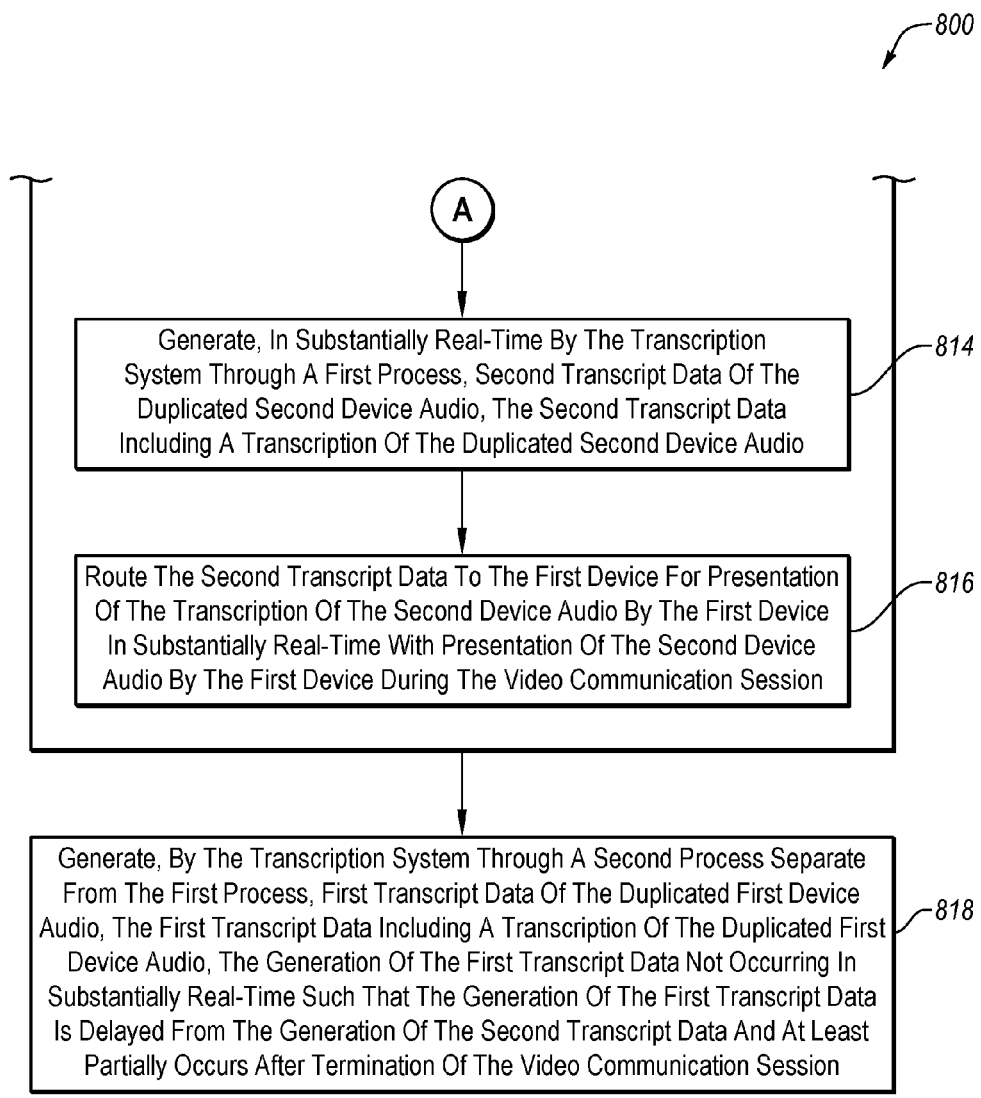

FIGS. 8a and 8b illustrate a flowchart of an example method 800 to transcribe communication sessions between devices. The method 800 may be arranged in accordance with at least one embodiment described in the present disclosure. The method 800 may be performed, in whole or in part, in some embodiments by a system or combinations of components in a system or environment as described in the present disclosure. For example, the method 800 may be performed, in whole or in part, by the communication system 130, the communication system 530, the communication system 1130, and/or the system 1700 of FIGS. 1, 5, 11, and 17, respectively. In these and other embodiments, some or all of the operations of the method 800 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 800 may begin at block 802, where a video communication session may be established between a first device and a second device using a communication system such that first device video and first device audio is sent from the first device to the second device and second device video and second device audio is sent from the second device to the first device.

In block 804, the first device audio and the second device audio may be received at the communication system.

In block 806, the first device audio and the second device audio may be duplicated by the communication system to generate duplicated first device audio and duplicated second device audio.

In block 808, second device audio may be routed by the communication system to the first device. In block 810, the first device audio may be routed by the communication system to the second device. In block 812, the duplicated first device audio and the duplicated second device audio may be separately routed by the communication system to a transcription system.

In block 814, second transcript data of the duplicated second device audio may be generated in substantially real-time by the transcription system through a first process. The second transcript data may include a transcription of the duplicated second device audio.

In block 816, the second transcript data may be routed to the first device for presentation of the transcription of the second device audio by the first device in substantially real-time with presentation of the second device audio by the first device during the video communication session.

In block 818, first transcript data of the duplicated first device audio may be generated by the transcription system through a second process separate from the first process. The first transcript data may include a transcription of the duplicated first device audio. The generation of the first transcript data may not occur in substantially real-time such that the generation of the first transcript data is delayed from the generation of the second transcript data and at least partially occurs after termination of the video communication session.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 800 may further include combining the first transcript data and the second transcript data to generate third transcript data that includes a combined transcription of the transcription of the first device audio and the transcription of the second device audio. In some embodiments, the first transcript data and the second transcript data may be interweaved to create the third transcript data such that the combined transcription included in the third transcript data is substantially in chronological order. In these and other embodiments, the first transcript data includes multiple first data segments. Each of the multiple first data segments may include a first time stamp and one or more first words in the transcription of the first device audio. In these and other embodiments, the second transcript data includes multiple second data segments. Each of the multiple second data segments includes a second time stamp and one or more second words in the transcription of the second device audio. In these and other embodiments, the first transcript data and the second transcript data may be interweaved based on the first time stamps of the first data segments and the second time stamps of the second data segments.

In some embodiments, the method 800 may further include obtaining a request for the video communication session at the communication system from a first device and in response to obtaining the request, selecting the second device from multiple second devices to participate in the communication session. In some embodiments, the method 800 may further include obtaining user data of a user associated with the first device from a server in the communication system. In some embodiments, the user data may include a medical condition of the user. In these and other embodiments, the method 800 may further include selecting the second device fr, the medical device 1170 may include a communication unit om the multiple second devices to participate in the communication session based on the medical condition of the user.

Figure 9:
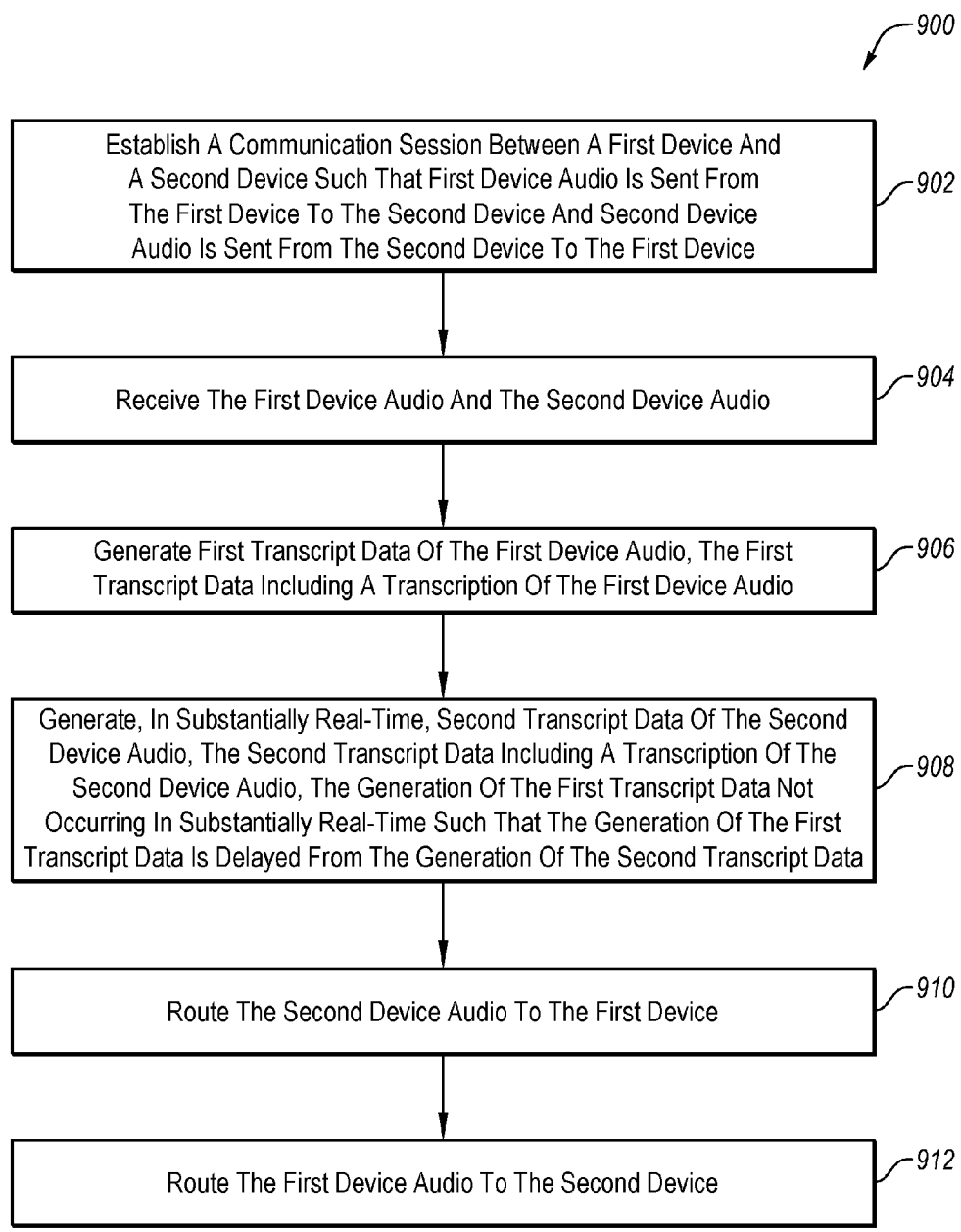
FIG. 9 is a flowchart of another example method to transcribe communication sessions between devices.

FIG. 9 is a flowchart of another example method 900 to transcribe communication sessions between devices. The method 900 may be arranged in accordance with at least one embodiment described in the present disclosure. The method 900 may be performed, in whole or in part, in some embodiments by a system or combinations of components in a system or environment as described in the present disclosure. For example, the method 900 may be performed, in whole or in part, by the communication system 130, the communication system 530, the communication system 1130, and/or the system 1700 of FIGS. 1, 5, 11, and 17, respectively. In these and other embodiments, some or all of the operations of the method 900 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 900 may begin at block 902, where a communication session between a first device and a second device may be established such that first device audio is sent from the first device to the second device and second device audio is sent from the second device to the first device. In some embodiments, the communication session may be a video communication session.

In block 904, the first device audio and the second device audio may be received. In block 906, first transcript data of the first device audio may be generated. The first transcript data may include a transcription of the first device audio.

In block 908, second transcript data of the second device audio may be generated in substantially real-time. The second transcript data may include a transcription of the second device audio. The generation of the first transcript data may not occur in substantially real-time such that the generation of the first transcript data is delayed from the generation of the second transcript data.

In block 910, the second device audio may be routed to the first device. In block 912, the first device audio may be routed to the second device.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 900 may further include duplicating the first device audio and the second device audio to generate duplicated first device audio and duplicated second device audio. In these and other embodiments, the first transcript data may be generated using the duplicated first device audio and the second transcript data may be generated using the duplicated second device audio.

In some embodiments, the method 900 may further include routing the second transcript data to the first device for presentation of the transcription of the second device audio by the first device in substantially real-time with presentation of the second device audio by the first device during the communication session.

In some embodiments, the method 900 may further include combining the first transcript data and the second transcript data to generate third transcript data that includes a combined transcription of the transcription of the first device audio and the transcription of the second device audio. In these and other embodiments, the first transcript data and the second transcript data may be interweaved to create the third transcript data such that the combined transcription included in the third transcript data is substantially in chronological order.

Figure 10:
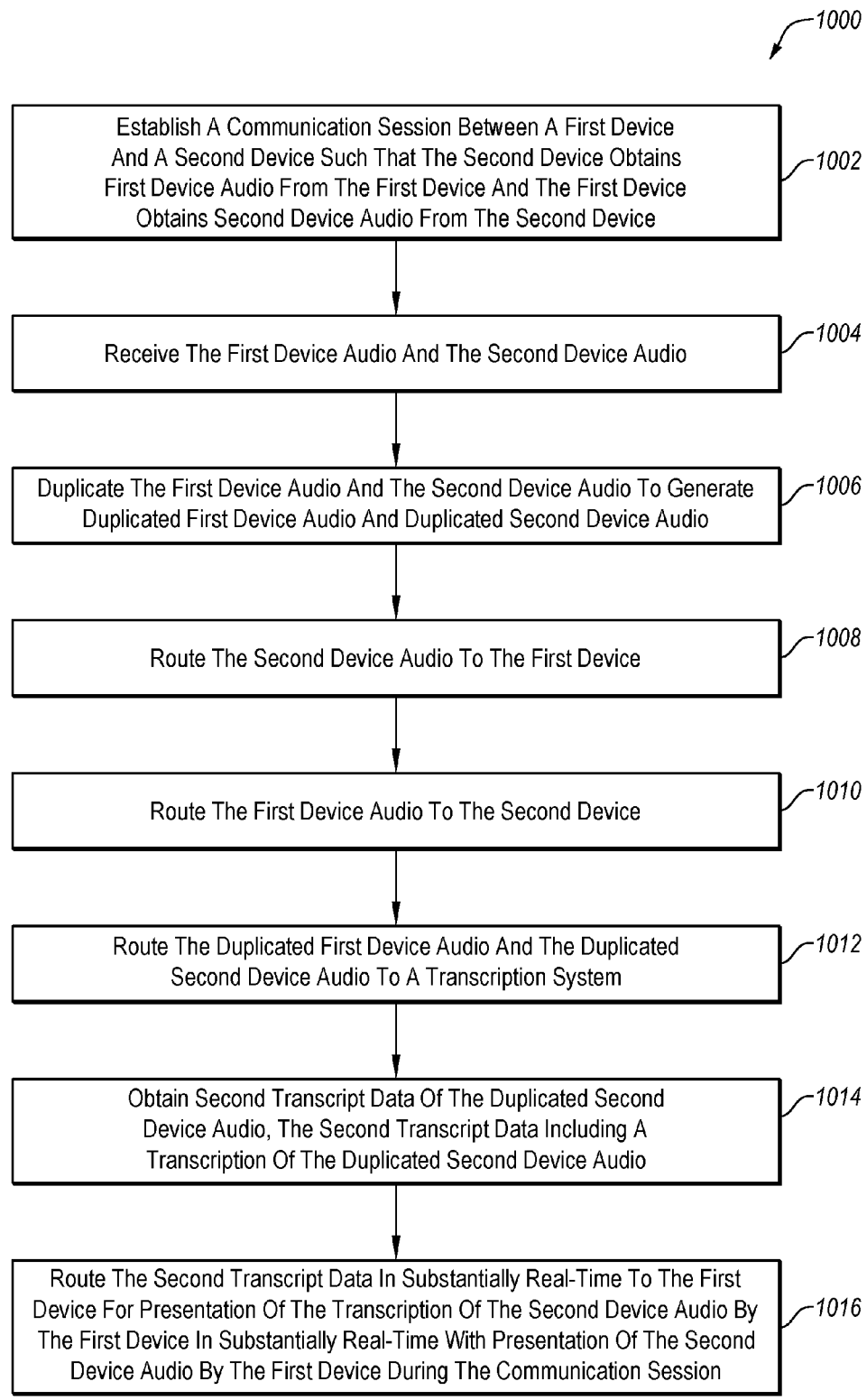
FIG. 10 is a flowchart of another example method to transcribe communication sessions between devices.

FIG. 10 is a flowchart of an example method 1000 to transcribe communication sessions between devices. The method 1000 may be arranged in accordance with at least one embodiment described in the present disclosure. The method 1000 may be performed, in whole or in part, in some embodiments by a system or combinations of components in a system or environment as described in the present disclosure. For example, the method 1000 may be performed, in whole or in part, by the communication system 130, the communication system 530, the communication system 1130, and/or the system 1700 of FIGS. 1, 5, 11, and 17, respectively. In these and other embodiments, some or all of the operations of the method 1000 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 1000 may begin at block 1002, where a communication session is established between a first device and a second device such that the second device obtains first device audio from the first device and the first device obtains second device audio from the second device.

In block 1004, the first device audio and the second device audio are received. In block 1006, the first device audio and the second device audio are duplicated to generate duplicated first device audio and duplicated second device audio.

In block 1008, the second device audio is routed to the first device. In block 1010, the first device audio is routed to the second device. In block 1012, the duplicated first device audio and the duplicated second device audio are routed to a transcription system.

In block 1014, second transcript data of the duplicated second device audio may be obtained. The second transcript data may include a transcription of the duplicated second device audio.

In block 1016, the second transcript data may be routed in substantially real-time to the first device for presentation of the transcription of the second device audio by the first device in substantially real-time with presentation of the second device audio by the first device during the communication session.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 1000 may further include obtaining a request for the communication session from a first device and in response to obtaining the request, selecting the second device from multiple second devices to participate in the communication session.

In some embodiments, the method 1000 may further include obtaining first transcript data of the first device audio. The first transcript data may include a transcription of the first device audio. In some embodiments, the method 1000 may further include routing the first transcript data to the second device for presentation of the transcription of the first device audio by the second device. In some embodiments, routing the first transcript data to the second device may occur after the communication session.

Figure 11:
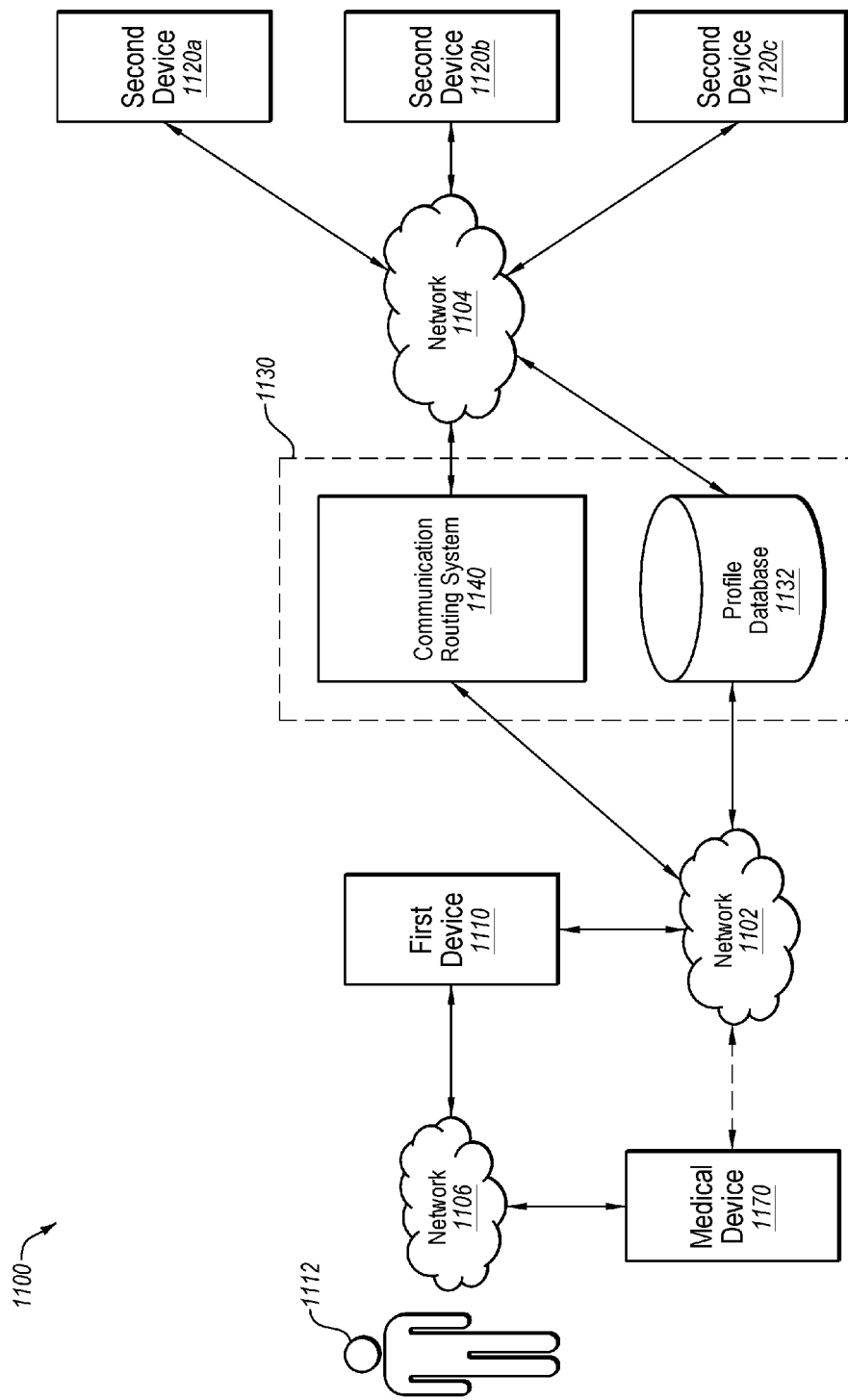
FIG. 11 illustrates another example environment related to device to device communication.

FIG. 11 illustrates another example environment 1100 related to device to device communication. The environment 1100 may be arranged in accordance with at least one embodiment described in the present disclosure. The environment 1100 may include a first network 1102; a second network 1104; a third network 1106; a first device 1110; a first user 1112; second devices 1120, including a first second-device 1120a, a second second-device 1120b, and a third second-device 1120c; a communication system 1130 that includes a profile database 1132, a communication routing system 1140; and a medical device 1170.

The first network 1102, the second network 1104, the first device 1110, the second devices 1120, and the communication system 1130, including the communication routing system 1140, and the profile database 1132, in some respects may be analogous to the first network 502, the second network 504, the first device 510, the second devices 520, and the communication system 530, including the communication routing system 540 and the profile database 532, of FIG. 5, respectively. Accordingly, limited or no further explanation may be provided with respect to certain aspects of one or more of these elements in the discussion of FIG. 11.

The third network 1106 may be configured to communicatively couple the first device 1110 and the medical device 1170. In some embodiments, the third network 1106 may be a local area network and the first network 1102 and the second network 1104 may be wide area networks. In these and other embodiments, the third network 1106 may be a wired or a wireless network. In some embodiments, the third network 1106 may include a Bluetooth® communication network, IEEE 802.11 wireless network, Universal Serial Bus (USB), among other types of local area networks.

The medical device 1170 may be any type of medical device configured to produce data regarding a health condition of the first user 1112. For example, the medical device 1170 may be configured to monitor one or more vital signs of the first user 1112. The vital signs may include a heart rate, blood pressure, temperature, respiratory rate, and blood oxygen level, among other vital signs of a user. In some embodiments, the medical device 1170 may be configured to monitor one or more other health conditions of the first user 1112. For example, the medical device 1170 may be configured to monitor a blood glucose level, weight, blood level counts, body composition (e.g., fat percentage, lean mass percentage, etc.) among health conditions.

In some embodiments, the medical device 1170 may include one or more sensors configured to monitor the vital signs or health condition of the first user 1112. Different sensors may be used to monitor the different vital signs or health condition. Alternatively or additionally, one or more sensors may be used to monitor multiple vital signs or health conditions. In some embodiments, the medical device 1170 may be configured to be worn by the first user 1112. Alternatively or additionally, the medical device 1170 may be positioned next to the first user 1112 and may include one or more elements that touch or with which the user may interact to monitor the vital signs or health conditions of the first user 1112.

In some embodiments, the medical device 1170 may include a communication unit to communicate over the third network 1106 with the first device 1110. Alternatively or additionally, the third network 1106 may not be a part of the environment 1100. In these and other embodiments, the medical device 1170 may communicate with the first device 1110 over the first network 1102 or a portion of the first network 1102. In some embodiments, the medical device 1170 may not directly communicate with the first device 1110. In these and other embodiments, the medical device 1170 may communicate with a server or other devices over the first network 1102. The first device 1110 may access the server or other device over the first network 1102 to communicate, receive data from, send instructions to, or otherwise interact with the medical device 1170.

An example of the interaction of the elements illustrated in the environment 1100 is now provided. As described below, the elements illustrated in the environment 1100 may interact to establish a communication session between the first device 1110 and one or more of the second devices 1120 and provide vital signs of the first user 1112 to the communication system 1130.

In some embodiments, the first device 1110 may obtain or include a communication address for sending communication requests to the communication system 1130. In these and other embodiments, the first device 1110 may be configured to receive input from the first user 1112 to send a request for a communication session to the communication system 1130.

For example, in some embodiments, the first device 1110 may be configured to present a user-interface on a display that includes one or more elements with which the first user 1112 may interact. The elements may be selectable icons, fields, buttons, or other user elements. The first device 1110 may obtain user input from the first user 1112 through interaction by the first user 1112 with the user-interface through a user-interface unit, such as a touch screen, trackpad, mouse, buttons, etc., of the first device 1110. In some embodiments, the first device 1110 may receive input from the first user 1112 to send a request for a communication session through movement of the first device 1110. For example, the first user 1112 may move the first device 1110 in a certain pattern that is recognized by the first device 1110 as a request to send a request for a communication session. Alternatively or additionally, the first device 1110 may receive audio input from the first user 1112 that directs the first device 1110 to send a request for a communication session.

In response to obtaining the request from the first user 1112 to request a communication session, the first device 1110 may also be configured to send a communication request to the communication system 1130 over the first network 1102. Alternatively or additionally, in response to obtaining the request from the first user 1112 to request a communication session, the first device 1110 may be configured to send vital sign data collected from the medical device 1170 to the communication system 1130 over the first network 1102.

In some embodiments, the first device 1110 may have obtained vital sign data from the medical device 1170 before the request is obtained from the first user 1112. For example, in some embodiments, the first device 1110 may obtain vital sign data from the medical device 1170 at different intervals. For example, the first device 1110 may obtain vital sign data at set intervals of time in response to particular events, such as changes in the vital signs from certain thresholds, requests from the first user 1112, the vital signs reaching certain thresholds, and power levels of the medical device 1170, among other events. In some embodiments, the first device 1110 may establish a communication link with the medical device 1170 over the third network 1106 to receive the vital sign data. Alternatively or additionally, the first device 1110 may obtain the vital sign data from another device over the first network 1102 or over the third network 1106.

In some instances in which the vital sign data is obtained before the request from the first user 1112, the first device 1110 may send the most current vital sign data, other vital sign data, or an aggregate of vital sign data previously collected, from the medical device 1170 to the communication system 1130 in response to the request from the first user 1112. For example, in these and other embodiments, the first device 1110 may obtain vital sign data generated by the medical device 1170 at certain periods before the request from the first user 1112.

In some embodiments, the vital sign data the first device 1110 may send to the communication system 1130 may depend on the frequency that the first device 1110 has previously provided vital sign data to the communication system 1130. For example, when the first device 1110 has not sent vital sign data over a threshold period, such as 1, 2, 5, 10, 20, 50, or 100 hours, the first device 1110 may send the current and previous vital sign data, and/or some aggregation of vital sign data. In these and other embodiments, the threshold period may be based on the health condition of the first user 1112, among other factors.

In some embodiments, in response to the request from the first user 1112, the first device 1110 may be configured to obtain vital sign data generated by the medical device 1170. In some embodiments, the first device 1110 may send a request for the current vital sign data. In some embodiments, the first device 1110 may send the request for the current vital sign data to the medical device 1170 over the third network 1106. Alternatively or additionally, the first device 1110 may send the request for the current vital sign data to another device over the first network 1102 or the third network 1106 that obtained the current vital sign data from the medical device 1170. In these and other embodiments, the other device may request the current vital sign data from the medical device 1170 and send the current vital sign data to the first device 1110.

In some embodiments, to obtain the current vital sign data generated by the medical device 1170, the first device 1110 may be configured to establish a communication link with the medical device 1170 over the third network 1106 in response to the request from the first user 1112. In these and other embodiments, the first device 1110 may send a request to establish the communication link to the medical device 1170. After establishing the communication link, the first device 1110 may request and obtain the current vital sign data from the medical device 1170. After obtaining the current vital sign data, the first device 1110 may send the current vital sign data to the communication system 1130.

As discussed, the first device 1110 may send the current vital sign data to the communication system 1130 in response to a request for the communication session from the first user 1112. The first device 1110 may also send a request for a communication session with one of the second devices 1120 to the communication system 1130.

In some embodiments, the first device 1110 may send the current vital sign data with the request for the communication session to the communication system 1130. For example, the first device 1110 may generate a request that includes packets of data that include the current vital sign data. In these and other embodiments, the first device 1110 may send the request for the communication session and the current vital sign data to the same communication address of the communication system 1130.

In some embodiments, the first device 1110 may send the current vital sign data to a different communication address of the communication system 1130 than the communication address to which a request for a communication session is sent. For example, in some embodiments, the first device 1110 may send the current vital sign data to the profile database 1132 of the communication system 1130. In these and other embodiments, the first device 1110 may send the request for the communication session to the communication routing system 1140. Both of the requests may be sent over the first network 1102 to the communication system 1130, but the request and the current vital sign data may be sent to different endpoints of the communication system 1130.

In some embodiments, the first device 1110 may be configured to send a communication request to the communication routing system 1140 in response to levels of received vital sign data from the medical device 1170. For example, the first device 1110 may be configured to obtain vital sign data at particular intervals. In these and other embodiments, when the current vital sign data varies from a threshold, the first device 1110 may be configured to send a request for a communication session to the communication routing system 1140.

In some embodiments, the threshold may be selected based on the medical condition of the user. In these and other embodiments, the threshold may be input by a health professional. For example, in response to a previous communication session, the communication system 1130 may send the threshold to the first device 1110. In these and other embodiments, the threshold may be selected by a health professional that participated in the previous communication session.

In some embodiments, the threshold may be selected based on previously obtained vital sign data. For example, the first device 1110 may obtain vital sign data for a period. Based on the vital sign data for the period, the threshold may be selected. For example, the threshold may be some number of standard deviations from the mean, medium, or other combination of the previously obtained vital sign data.

By providing the current vital sign data to the communication system 1130, the communication routing system 1140 may make a selection of one of the second devices 1120 to participate in the communication session based on the current vital sign data. In some embodiments, using current vital sign data may change the selection of the one of the second devices 1120. Thus, providing the current vital sign data, in some embodiments, may improve a user experience of the first user 1112. Alternatively or additionally, providing the current vital sign data may reduce network usage and communication connections because the communication routing system 1140 may select a device for the communication session that is more adequately suited for the communication session which may reduce a number of transfers between devices to select an appropriate device for the communication session. A device may be more adequately suited for the communication session based on the device being associated with a second user that is suited for the communication session with the first device.

As described, the first device 1110 may send the request for the communication session to the communication system 1130. In some embodiments, the first device 1110 may send the communication request to a communication address of the communication system 1130. The communication address may be an endpoint of the communication routing system 1140.

The communication routing system 1140 may be configured to obtain the request for the communication session and to determine how to handle the request for the communication session. In some embodiments, to determine how to handle the request for the communication session, the communication routing system 1140 may analyze the request. In some embodiments, the request may include an address for another device or system with which the communication session may be established. In these and other embodiments, the communication routing system 1140 may follow a procedure to route the request to the appropriate device or system or establish a communication session with the appropriate device or system.

In some embodiments, the request may not include an address for another device or system with which the communication session may be established. In these and other embodiments, the communication routing system 1140 may obtain additional information to assist the communication routing system 1140 in selecting a device or system to participate in the communication session with the first device 1110.

For example, in some embodiments, the communication routing system 1140 may obtain information about the first user 1112. The information about the first user 1112 may be obtained from the first device 1110. Alternatively or additionally, the information about the first user 1112 may be obtained from the profile database 1132 or another system. The information obtained from either the profile database 1132 and/or the first device 1110 may include profile data of the first user 1112, current and/or past vital sign data of the user, among other data. The profile data of the first user 1112 may include a location of the user, such as a residence of the user, a medical condition of the user, transcripts or portions of transcripts from past communication sessions, environmental conditions surrounding the first device, user preferences, user conditions, insurance information of the user, and vital sign thresholds, among other information about the user.

In some embodiments, the communication routing system 1140 may analyze the current vital sign data to determine a health status of the first user 1112 as explained below. Based on the health status of the first user 1112, the communication routing system 1140 may determine to establish the communication session with one of the second devices 1120, a third device, and/or an emergency response system or system associated with emergency personnel.

For example, in response to the health status of the first user 1112 indicating that in-person care of the user may be advisable instead of a communication session, the communication routing system 1140 may attempt to establish a communication session with an emergency response system, such as a 911 system in the United States. In these and other embodiments, the request for the communication session may be a video and audio request for a communication session. The communication routing system 1140 may establish an audio communication session with the emergency response system without video.

Alternatively or additionally, in response to the health status of the first user 1112 indicating that in-person care of the user may be advisable instead of a communication session, the communication routing system 1140 may attempt to establish a communication session with a third system or device, such as medical personnel associated with the first user 1112. For example, a doctor(s) or other medical personnel may have been assigned to assist the first user 1112. In these and other embodiments, a communication session may be established with a third system or device associated with the doctor(s) or other medical personnel.

In these and other embodiments, the health status of the first user 1112 may be determined by comparing the vital sign data of the first user 1112 to first threshold vital signs. The first threshold vital signs for each vital sign may include a lower and an upper boundary. When the vital sign data of the first user 1112 is outside the first threshold vital signs, the health status of the first user 1112 may indicate that in-person care of the user may be advisable instead of a communication session. The vital sign data may be outside the first threshold vital signs when the vital signs are above or below the first threshold vital signs. For example, for temperature, the first threshold vital signs may be 96.5 degrees and 101 degrees Fahrenheit. When the vital sign data is below 96.5 or above 101, the vital sign data may be outside the first threshold vital signs. When the vital sign data is between 96.5 and 101, the vital sign data may be inside the first threshold vital signs.

In some embodiments, the first threshold vital signs may be determined based on one or more of the following: on the demographics of the first user 1112, the medical condition of the first user 1112, previous vital sign data of the first user 1112, medical history of the first user 1112, and general medical knowledge, among other factors. In some embodiments, first threshold vital signs may be set by a healthcare professional. For example, a user of one of second devices may set the first threshold vital signs through one of the second devices 1120 communicating through the communication system 1130.

In some embodiments, the current vital sign data may be used to prioritize a communication session between the first device 1110 and one of the second devices 1120. In these and other embodiments, the current vital sign data may be compared to second threshold vital signs. When the current vital sign data is outside the second threshold vital signs, the communication session may be prioritized. The second threshold vital signs may be determined based on the same factors as the first threshold vital signs. In some embodiments, the second threshold vital signs may fall within the range of the first threshold vital signs. For example, the first threshold vital signs may be between 96.5 and 101, as such, the second threshold vital signs may be between 97.5 and 100, such that the second threshold vital signs fall within the lower and upper bounds of the first threshold vital signs.

In some embodiments, to prioritize a communication session between the first device 1110 and the second devices 1120, the second device selected for the communication session, referred to hereafter as the selected second device 1120, may be one of the second devices 1120 that are currently available to participate in a communication session. In these and other embodiments, each of the second devices 1120 may report a status to the communication system 1130. The status may indicate if the second devices 1120 and users of the second devices 1120 are available for a communication session. Using the status information, the communication routing system 1140 may determine the selected second device from among the second devices 1120 that are currently available.

In some embodiments, the communication routing system 1140 may determine the selected second device from among the second devices 1120 based on other criteria. The other criteria may include one or more of the following: a location of the first user 1112, a medical condition of the first user 1112, transcripts or portions of transcripts of previous communication sessions between the first device 1110 and the second devices 1120, financial considerations, environmental conditions outside the first device 1110, previous communication sessions between the first device 1110 and the second devices 1120, and preferences of the first user 1112, among other criteria. Each of the above criteria is discussed further during the discussion of FIG. 12.

In some embodiments, one or more of the criteria used to determine the selected second device from among the second devices 1120 may be based on information of a second user that is associated with the selected second device. In these and other embodiments, determining the selected second device may be based on matching criteria of the first user 1112 with a profile of a second user that is associated with the selected second device such that a communication session is established between the first device 1110 and the selected second device to allow the first user 1112 to communicate with a second user that may be qualified to assist the first user 1112. In these and other embodiments, each of the second devices may be described as including particular criteria. A second device may be described as including particular criteria if a second user associated with the second device includes that particular criteria.

One or more criteria may be selected to determine the selected second device. For example, in some embodiments, multiple criteria may be used to determine the selected second device. Alternatively or additionally, less than all of the multiple criteria discussed may be used to determine the selected second device. In these and other embodiments, one or more of the criteria may be optional criteria. The optional criteria may be selected based on preferences of the first user 1112, fees paid for a communication session, a number of communication sessions participated in by the first user 1112, and network traffic being experienced by the communication routing system 1140, among other factors.

In these and other embodiments, the communication routing system 1140 may include information concerning the second devices 1120 for each of the selected criteria. Alternatively or additionally, the communication routing system 1140 may not include information concerning the second devices 1120 for one or more selected criteria that are optional criteria. In these and other embodiments, when the communication routing system 1140 does not include information for a particular second device with respect to a particular selected criteria it may be determined that the second device does not meet the particular selected criteria. Alternatively or additionally, for a particular selected criteria, it may be determined that a particular second device meets the particular selected criteria even when the communication routing system 1140 does not include information for the particular second device.

In some circumstances, the selected criteria may be such that none of the second devices 1120 may meet the selected criteria. In these and other embodiments, one or more of the selected criteria may be removed until one of the second devices 1120 meets the selected criteria. The order of removal of the selected criteria may be random or based on settings in the system. In some embodiments, certain criteria may not be removed, such as a location of the first user 1112, a medical condition of the first user 1112, and financial considerations, among other criteria.

In some embodiments, the second devices 1120 may be culled individually based on the selected criteria. For example, the second devices 1120 may be culled based on a first selected criteria to determine a first set of second devices that meet the first selected criteria. The first set of second devices may be culled based on a second selected criteria to determine a second set of second devices that meet the first and the second selected criteria. The second set of second devices may be further culled based on a third selected criteria to determine a third set of second devices that meet the first, second, and third selected criteria. The described process may continue until the second devices have been culled for all of the selected criteria. Alternatively or additionally, the described process may continue until the culling of the second devices indicates that none of the second devices meet the selected criteria. In these and other embodiments, one of the second devices from the last set of second devices may be selected as the selected second device. The order of the selected criteria used for culling may change based on preferences of the first user 1112, vital signs of the first user 1112, network traffic of the communication system 1130, and governmental regulations, among other factors.

Modifications, additions, or omissions may be made to the environment 1100 without departing from the scope of the present disclosure. For example, in some embodiments, the medical device 1170 may be part of the first device 1110. Alternatively or additionally, the profile database 1132 may be part of the communication routing system 1140 or may be outside the communication system 1130.

As another example, a selection among second users instead of second devices may be determined based on the criteria as described above. Based on the selection of a second user, a second device associated with the selected second user may then be selected. As a result, the communication routing system 1140, even if selecting among second user, may ultimately select a second device based on criteria for a communication session. In these and other embodiments, the selection may be performed with respect to criteria that relates specifically to a second device or is associated with the second device based on a second user that is associated with the second device.

Figure 12A:
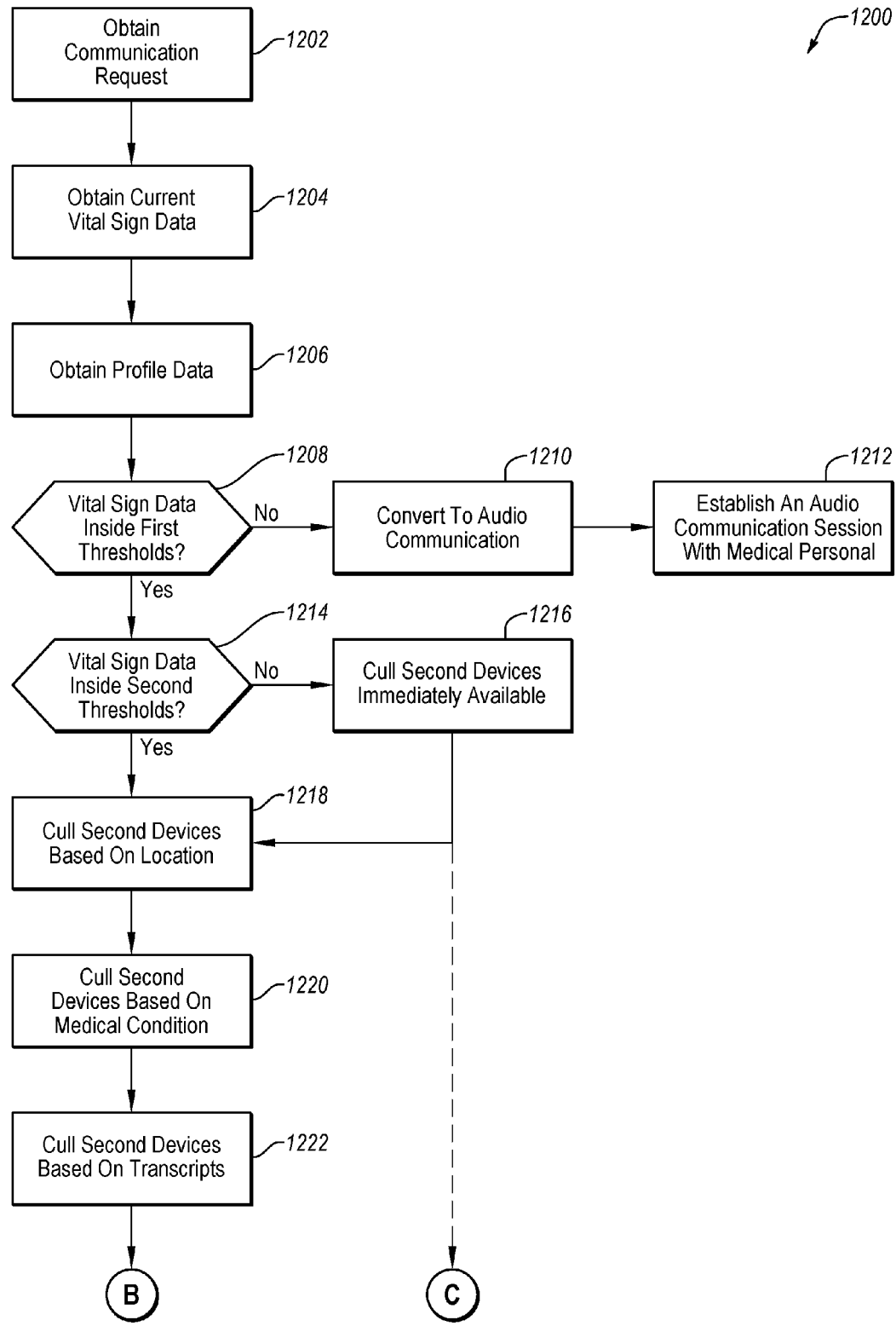
FIGS. 12a and 12b illustrate a flowchart of an example method to select a device for a communication session.
Figure 12B:
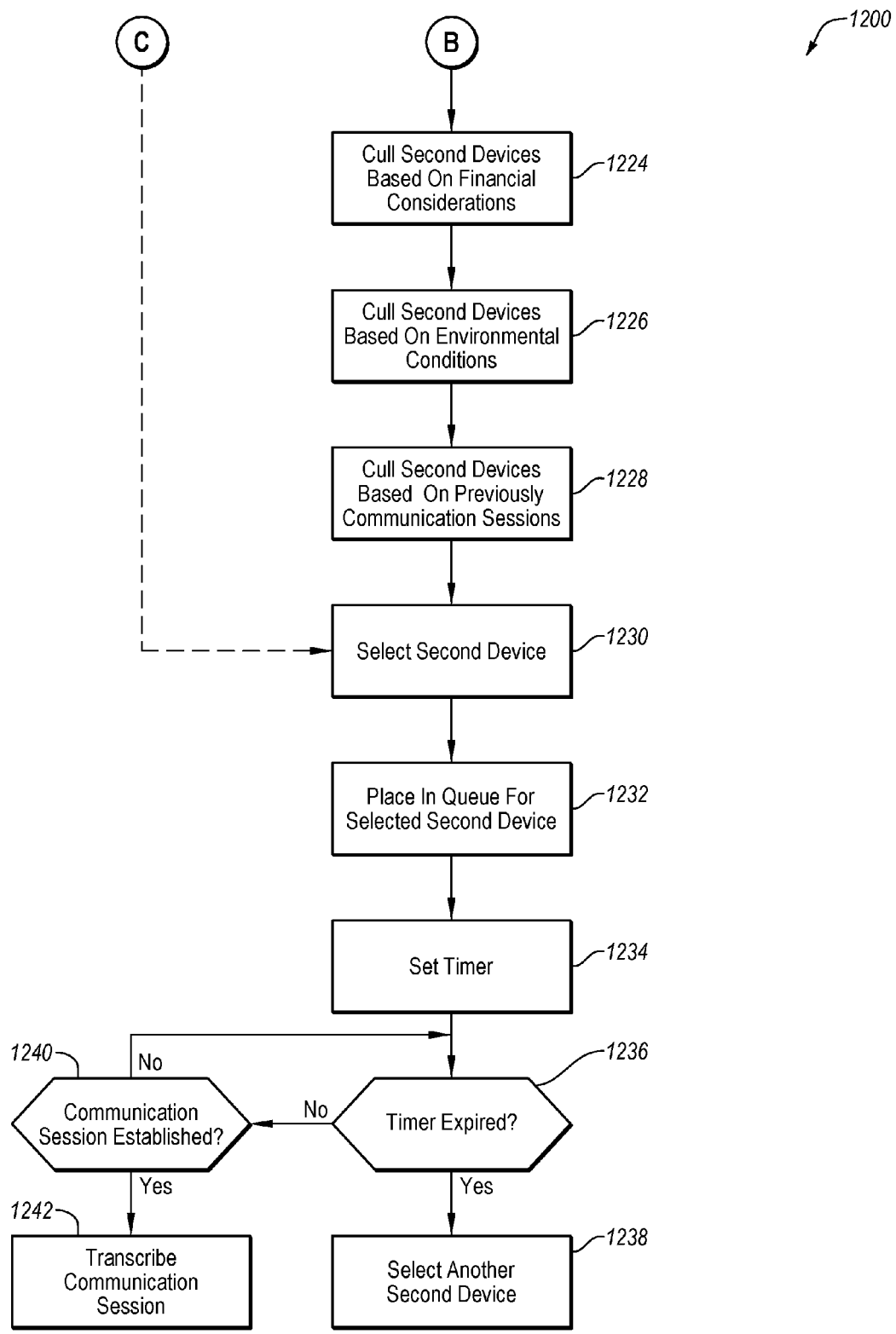

FIGS. 12a and 12b illustrate a flowchart of an example method 1200 to select a device for a communication session. The method 1200 may be arranged in accordance with at least one embodiment described in the present disclosure. The method 1200 may be performed, in whole or in part, in some embodiments by a system or combinations of components in a system or environment as described in the present disclosure. For example, the method 1200 may be performed, in whole or in part, by the communication system 130, the communication system 530, the communication system 1130, and/or the system 1700 of FIGS. 1, 5, 11, and 17, respectively. In these and other embodiments, some or all of the steps of the method 1200 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 1200 may begin at block 1202, where a request to establish a communication session may be obtained from a first device associated with a user. The request may be obtained by a communication system configured to establish and maintain a communication session between a first device and a second device selected by the communication system. In these and other embodiments, the request to establish the communication session may not include a designation of a second device that may participate in the communication session. In these and other embodiments, the second devices may be devices associated with the communication system. The second devices may each be associated with health personnel that may communicate with the user over the communication session.

In block 1204, current vital sign data of the user may be obtained. In some embodiments, the current vital sign data may be obtained from a medical device that includes sensors that obtained data to generate the current vital sign data. Alternatively or additionally, the current vital sign data may be obtained from another device that obtains the current vital sign data from the medical device.

In block 1206, profile data of the user may be obtained. In some embodiments, obtaining the profile data may include obtaining the profile data of the user from a profile database. The profile data may include multiple aspects of information about the user. For example, the profile data may include a location of the user, such as a residence of the user. In some embodiments, the profile data may also include a medical condition of the user, transcripts or portions of transcripts from past communication sessions, environmental conditions surrounding the first device, user preferences, user conditions, vital sign thresholds, and insurance information of the user, among other information about the user.

In block 1208, it may be determined whether the vital sign data is inside of one or more first thresholds. The first thresholds may be set such that the health status of the individual is at a level that in-person care of the user may be advisable instead of a communication session through the communication system. The first thresholds may be determined based on one or more of the following: on the demographics of the user, the medical condition of the user, previous vital sign data of the user, and general medical knowledge, among other factors. For example, when the vital sign data includes a heart rate, the first thresholds may include an upper and lower boundary, such as between 45 and 120 beats per minute. When the vital sign data indicates that the heart rate is outside the first thresholds, the method may proceed to block 1210. For example, when the heart rate of the user is less than 45 beats per minute or more than 120 beats per minute, the heart rate of the individual may be outside the first thresholds. When the vital sign data indicates that the heart rate is inside the first thresholds, the method may proceed to block 1214. For example, when the heart rate of the individual is between 45 and 120 beats per minute, the heart rate of the individual may be inside the first thresholds.

In block 1210, the communication request may be converted to an audio communication request. In these and other embodiments, the communication request as received by the communication system may be a video and audio communication request. In these and other embodiments, the communication system may establish just the audio portion of the communication request.

In block 1212, an audio communication session with medical personnel may be established. In some embodiments, the medical personnel may be first responders of a governmental emergency response agency. For example, the communication system may establish the audio communication session with an emergency response agency, such as the 911 system, a police agency, or other agency. Alternatively or additionally, the medical personnel may be a medical doctor, hospital, or other medical personnel that are associated with the user. In these and other embodiments, the medical personnel may be different than the medical personnel with which the communication session regularly establishes a communication session, such as one of the second devices as discussed in FIGS. 1, 5, and 11.

In block 1214, it may be determined whether the vital sign data is inside one or more second thresholds. The second thresholds may be set such that the health status of the individual is at a level that the request for the communication session may be given priority over other communication sessions. The second thresholds may be determined based on one or more of the following factors: the demographics of the user, the medical condition of the user, previous vital sign data of the user, and general medical knowledge, among other factors. For example, when the vital sign data includes a heart rate, the second thresholds may include an upper and lower boundary, such as between 60 and 100 beats per minute. In response to the vital sign data indicating that the heart rate is outside the second thresholds, the method may proceed to block 1216. For example, when the heart rate of the user is less than 60 beats per minute or more than 100 beats per minute, the heart rate of the individual may be outside the second thresholds. When the vital sign data indicates that the heart rate is inside the second thresholds, the method may proceed to block 1218. For example, when the heart rate of the individual is between 60 and 100 beats per minute, the heart rate of the individual may be inside the second thresholds.

In block 1216, the second devices may be culled to determine second devices that are immediately available for a communication session. For example, in these and other embodiments, the second devices may provide status updates to the communication system. The communication system may make this determination based on the status updates.

In block 1218, the second devices may be further culled based on the location of the user. For example, in some areas, such as the United States, health care professionals may be registered to provide services in a region, such as a state in the United States. In these and other embodiments, the second devices may be selected based on which of the users of the second devices are registered to provide health care in the location of the user. In these and other embodiments, the information about the users of the second devices and/or information about the second devices may be obtained by the communication system. For example, the information may be obtained from database. Alternatively or additionally, the information may be obtained previously and stored in a database. In these and other embodiments, a search request with the criteria from the profile data may be provided to the database to cull the database for the second devices or users of the second devices that match the criteria.

In block 1220, the second devices may be further culled based on the medical condition of the user. In these and other embodiments, the second devices may be selected based on which of the users of the second devices have skills and/or knowledge regarding the medical condition of the user.

In block 1222, the second devices may be further culled based on transcripts of previous communication sessions. In these and other embodiments, transcripts of the previous communication sessions may include information, such as preferences of the user, current medical conditions of the user, health plans, and treatment plans, among other information. In these and other embodiments, the second devices may be selected based on which of the users of the second devices have skills and/or knowledge regarding information from the transcripts of the previous communication sessions.

For example, in some embodiments, the transcripts of previous communication sessions may be parsed. The parsed communication sessions may be searched for particular phrases and keywords. The information surrounding the phrases or keywords may be the basis for culling the second devices. As another example, the transcripts of previous communication sessions may be searched for particular keywords. When the keywords are identified, the keywords may be associated with the user, such as by being added to the profile data associated with the user.

For example, during a previous communication session, a health care professional may describe a particular medical treatment and/or condition of the user that may not be part of the profile data of the user as the treatment or condition was not relevant when the profile data was obtained by the communication system. In these and other embodiments, a search for keywords that include a particular medical treatment or medical conditions, may be performed on transcripts of previous communication sessions. The particular medical treatment and/or condition discussed in the previous communication session may be matched to the keywords. The matched keywords may be added to the profile data of the user and used to select among the second devices.

In block 1224, the second devices may be further culled based on financial considerations. For example, the financial considerations may include how much the user or an insurer is contracted to pay for a communication session. For example, the users of the second devices may be compensated at different amounts. Accordingly, second devices may be selected based on the second devices having a cost basis that is appropriate for a contracted payment for the communication session, or a cost basis as determined by the communication system. For example, the communication system may select lower compensated users of the second devices over higher compensated users of the second devices based on a pay arrangement between the communication system and the users of the second devices.

In some embodiments, the financial considerations may involve selecting a second device associated with a user that is contracted with an insurer. For example, the user of the first device may have a first insurer. Various users of the second devices may be contracted with the first insurer to provide service while others of the users of the second devices may not be contracted with the first insurer to provide service. In these and other embodiments, the second devices with users contracted with the insurers may be selected.

In block 1226, the second devices may be further culled based on the environmental conditions surrounding the first device. In these and other embodiments, the second devices may be selected based on which of the users of the second devices include the capacity to handle the environment conditions surrounding the first device. For example, the first device may be in a low light environment. As a result, video captured by the first device may be difficult to see by a user of the second devices. Thus, users of the second devices may be selected that are able to handle low light video. As another example, the user of the first device may have a soft or high voice. As a result, audio captured by the first device may be difficult to hear by some of the users of the second devices. Thus, the users of the second devices may be selected that are able to understand the soft or high voice of the user of the first device based on profile data of the users of the second devices.

In block 1228, the second devices may be further culled based on previous communication sessions. In these and other embodiments, the second devices may be selected based on which of the users of the second devices with whom the first user previously interacted during a communication session. In these and other embodiments, a preference or rating score provided by a user after a previous communication session with a user of the second device may be considered. For example, if the user previously interacted with a particular user of a second device, but indicated that the interaction was unsatisfactory, the second device of the particular user may not be selected. As another example, if the user previously interacted with a particular user of a second device, and indicated that the interaction was satisfactory, the second device of the particular user may be selected.

In block 1230, a second device may be selected from the second devices. In these and other embodiments, when there is more than one second device available after the culling of the second devices, any one of the remaining second devices may be selected. Alternatively or additionally, when there is more than one second device available after the culling of the second devices, the second device with a shortest estimated response time may be selected. Alternatively or additionally, when there is more than one second device available after the culling of the second devices, the second device may be selected based on one or more other criteria, such as networking speed, work allotment, among other criteria.

In some embodiments, when no second device meets the criteria, one or more of the criteria for culling the second devices may be removed to determine a set of second devices for selection. In these and other embodiments, a second device that meets fewer criteria may be selected. Additional criteria may be removed until a second device may be selected. In some embodiments, the criteria may be removed in the order that the criteria are introduced. In some embodiments, the criteria may be removed in the order that they are introduced based on an importance of the criteria. For example, in some embodiments, criteria that is more important may be introduced first. For example, criteria related to adherence to laws, such as location of the user of the first device, may be presented first and may not be removed to select a second device. Thus, criteria that are less important or may be removed may be removed first to determine a set of second devices for selection.

In block 1232, after selection of the second device, the communication session with the first device may be placed in a queue for establishing a communication session with the second device.

In block 1234, a timer may be set. The timer may be set to a particular time that may be allowed for the user of the first device to wait for a communication session to be established. The time to wait for a communication session may be based on the medical condition of the user, financial considerations, among other criteria.

In block 1236, it may be determined whether the timer has expired. When the timer has not expired, the method 1200 may proceed to block 1240. When the timer has expired, the method 1200 may proceed to block 1238.

In block 1238, another second device may be selected. In some embodiments, when no other second device meets the criteria, one or more of the criteria for culling the second devices may be removed. In these and other embodiments, a second device that meets fewer criteria may be selected. Additional criteria may be removed until a second device may be selected.

In block 1240, it may be determined if a communication session has been established with the selected second device. A communication session may be established after the selected second device sends an indication obtained from a user of the selected second device that a communication session is established. Alternatively or additionally, the communication session may be established after the selected second device sends audio and/or video to the first device. When the communication session has been established, the method 1200 may proceed to block 1242. When the communication session has not been established, the method 1200 may proceed to block 1236.

In block 1242, the communication session may be transcribed. For example, transcript data may be generated for one or more of the audio streams in the communication session as described previously in this disclosure.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, in block 1216 when the vital sign data indicates that the heart rate is inside the second thresholds, the method 1200 may proceed to block 1230 instead of block 1218. In these and other embodiments, at block 1230, a second device of the immediately available second devices may be selected. In these and other embodiments, the further culling of the second devices performed in blocks 1218, 1220, 1222, 1224, 1226, and 1228 may not be performed. In these and other embodiments, the further culling of the second devices may not occur to more quickly establish a communication session between the first device and the selected second device. Alternatively or additionally, one or more of the blocks 1218, 1220, 1222, 1224, 1226, and 1228 may be performed between the block 1218 and the block 1230.

For example, in some embodiments, the method 1200 may further include culling the second devices based on preferences of the user. The preferences of the user may include a preferred language of the user. For example, the user may prefer to communicate in English. In these and other embodiments, the second devices may be culled based on the users of the second devices being able to communicate in English. As another example, the user may prefer to communicate with females. In these and other embodiments, the second devices may be culled based on the sex of the users of the second devices.

As another example, in some embodiments, the blocks 1218, 1220, 1222, 1224, 1226, and 1228, among others may be performed through a single operational request. For example, the culling criteria may be set and the second devices may be culled to determine the devices that meet the culling criteria. For example, in some embodiments, the second devices may be culled after each of the blocks 1218, 1220, 1222, 1224, 1226, and 1228. In these and other embodiments, a set of second devices may be determined after each of the blocks 1218, 1220, 1222, 1224, 1226, and 1228. The set of the second devices produced by one of the blocks 1218, 1220, 1222, 1224, 1226, and 1228 may be used in a subsequent block. For example, a first set of second devices may be determined after block 1218. The first set of second devices may be culled by block 1220 to determine a second set of second devices. The second set of second devices may be culled by block 1222 to determine a third set of second devices.

In some embodiments, when no second devices meet the criteria after a culling in one of the blocks 1218, 1220, 1222, 1224, 1226, and 1228, the method 1200 may proceed to block 1230. For example, if no second device meets the criteria after culling in block 1224, the set of second devices that meet the criteria from block 1222 may be used as the second devices in block 1230. In these and other embodiments, the blocks 1224, 1226, and 1228 may not be performed.

Alternatively or additionally, one or more of the blocks 1218, 1220, 1222, 1224, 1226, and 1228 may be performed through a single operational request. For example, the criteria may be set from each of the blocks 1218, 1220, 1222, 1224, 1226, and 1228 and the second devices may be culled based on all of the criteria. As another example, the criteria may be set from the blocks 1218, 1220, 1222, and the second devices may be culled based on all of the criteria. After which, the criteria may be set from the block 1224 and the second devices may be culled based on all of the criteria. In these and other embodiments, if there are still multiple second devices, the remaining second devices may be culled based on the criteria from the block 1228. Other combinations of the blocks 1218, 1220, 1222, 1224, 1226, and 1228, along with other culling information may be used to cull the second devices to select the second device for the communication session with the first device.

Figure 13:
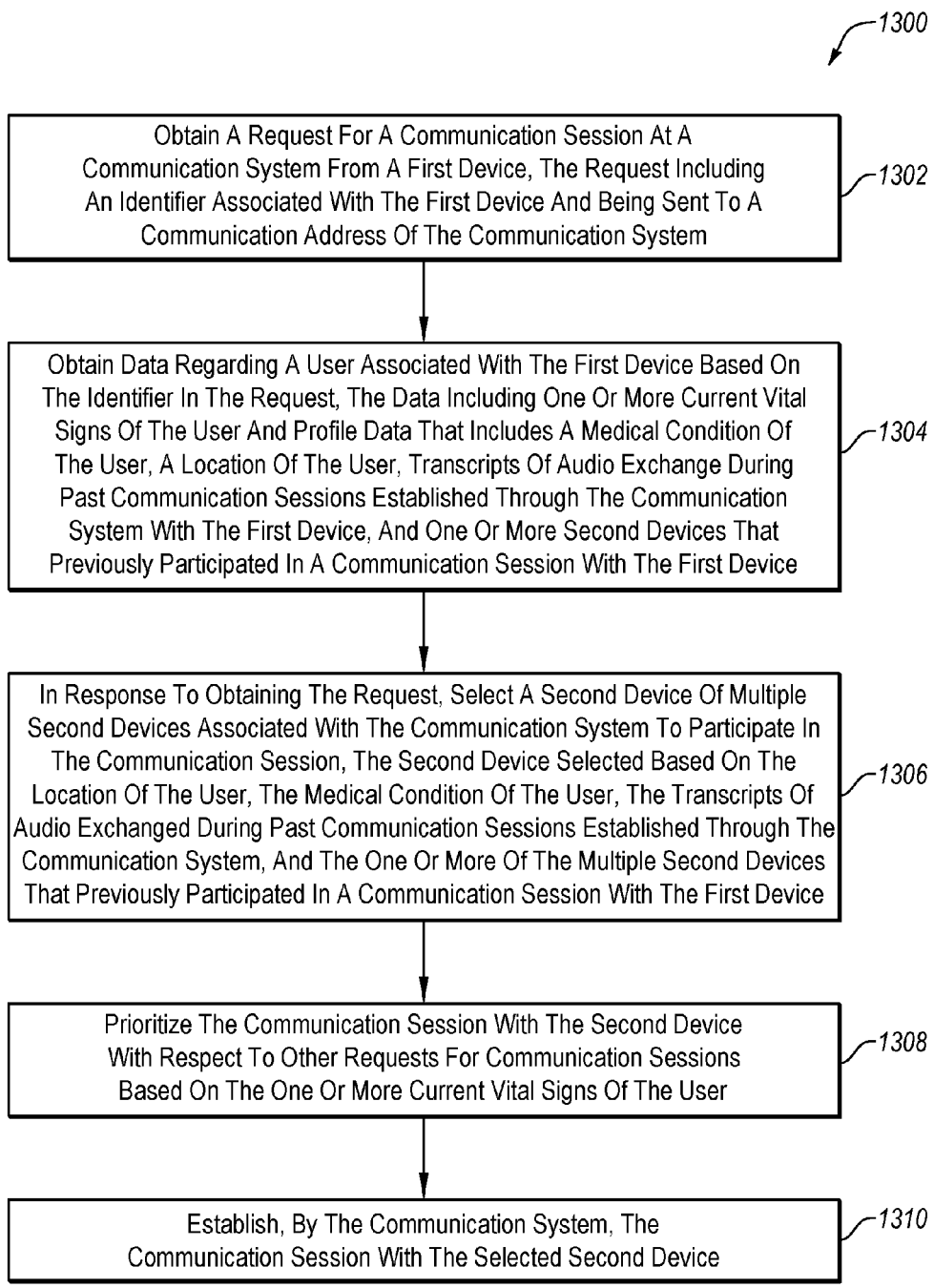
FIG. 13 is a flowchart of another example method to select a device for a communication session.

FIG. 13 is a flowchart of another example method 1300 to select a device for a communication session. The method 1300 may be arranged in accordance with at least one embodiment described in the present disclosure. The method 1300 may be performed, in whole or in part, in some embodiments by a system or combinations of components in a system or environment as described in the present disclosure. For example, the method 1300 may be performed, in whole or in part, by the communication system 130, the communication system 530, the communication system 1130, and/or the system 1700 of FIGS. 1, 5, 11, and 17, respectively. In these and other embodiments, some or all of the operations of the method 1300 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 1300 may begin at block 1302, where a request for a communication session may be obtained at a communication system from a first device. The request may include an identifier associated with the first device and being sent to a communication address of the communication system.

In block 1304, data regarding a user associated with the first device based on the identifier in the request may be obtained. The data may include one or more current vital signs of the user and profile data that includes: a medical condition of the user, a location of the user, transcripts of audio exchange during past communication sessions established through the communication system with the first device, and one or more second devices that previously participated in a communication session with the first device. In some embodiments, the profile data may further include environmental conditions surrounding the first device. In these and other embodiments, the second device may be selected based on the environmental conditions surrounding the first device.

In block 1306, in response to obtaining the request, a second device of multiple second devices associated with the communication system may be selected to participate in the communication session. The second device may be selected based on the location of the user, the medical condition of the user, the transcripts of audio exchanged during past communication sessions established through the communication system, and the one or more of the multiple second devices that previously participated in a communication session with the first device. In some embodiments, selecting the second device is performed without receiving additional data from the first device after obtaining the request for the communication session.

In some embodiments, the second device of the multiple second devices is further selected based on a cost associated with health professionals associated with the multiple second devices. In these and other embodiments, each of the multiple second devices may be associated with at least one health professional.

In block 1308, the communication session with the second device may be prioritized with respect to other requests for communication sessions based on the one or more current vital signs of the user. In block 1310, the communication session with the selected second device may be established by the communication system.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 1300 may further include providing the medical condition of the user to the second device after selecting the second device. In these and other embodiments, in response to obtaining the request and before selecting the second device, the method 1300 may further include comparing the one or more current vital signs of the user with one or more threshold vital signs. In these and other embodiments, in response to the one or more current vital signs of the user being consistent with the one or more threshold vital signs, the second device may be selected instead of routing the request for the communication session to an emergency response system.

Figure 14:
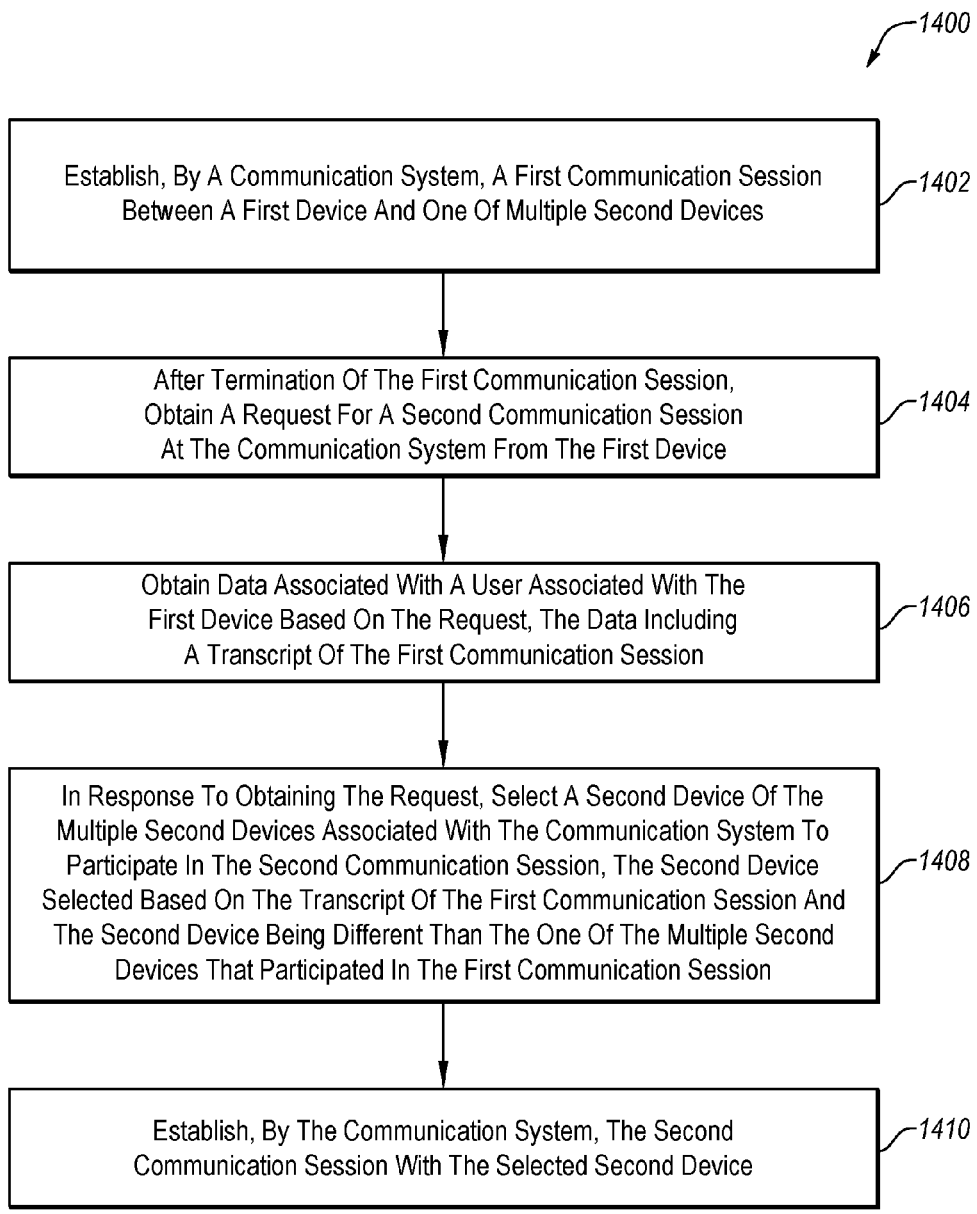
FIG. 14 is a flowchart of another example method to select a device for a communication session.

FIG. 14 is a flowchart of another example method 1400 to select a device for a communication session. The method 1400 may be arranged in accordance with at least one embodiment described in the present disclosure. The method 1400 may be performed, in whole or in part, in some embodiments by a system or combinations of components in a system or environment as described in the present disclosure. For example, the method 1400 may be performed, in whole or in part, by the communication system 130, the communication system 530, the communication system 1130, and/or the system 1700 of FIGS. 1, 5, 11, and 17, respectively. In these and other embodiments, some or all of the operations of the method 1400 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 1400 may begin at block 1402, where a first communication session may be established by a communication system between a first device and one of multiple second devices. In block 1404, after termination of the first communication session, a request for a second communication session may be obtained at the communication system from the first device.

In block 1406, data associated with a user associated with the first device based on the request may be obtained. The data may include a transcript of the first communication session. In these and other embodiments, the data may further include one or more vital signs of the user. In these and other embodiments, the method 1400 may further include prioritizing the communication session with respect to other requests for communication sessions based on the one or more vital signs of the user.

In block 1408, in response to obtaining the request, selecting a second device of the multiple second devices associated with the communication system to participate in the second communication session, the second device may be selected based on the transcript of the first communication session and the second device being different than the one of the multiple second devices that participated in the first communication session.

In block 1410, the second communication session may be established by the communication system with the selected second device. In some embodiments, the data may further include a medical condition of the user. In these and other embodiments, the method 1400 may further include selecting the second device based on the medical condition of the user. In some embodiments, the data may further include a location of the user. In these and other embodiments, the method 1400 may further include selecting the second device based on the location of the user.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

Figure 15:
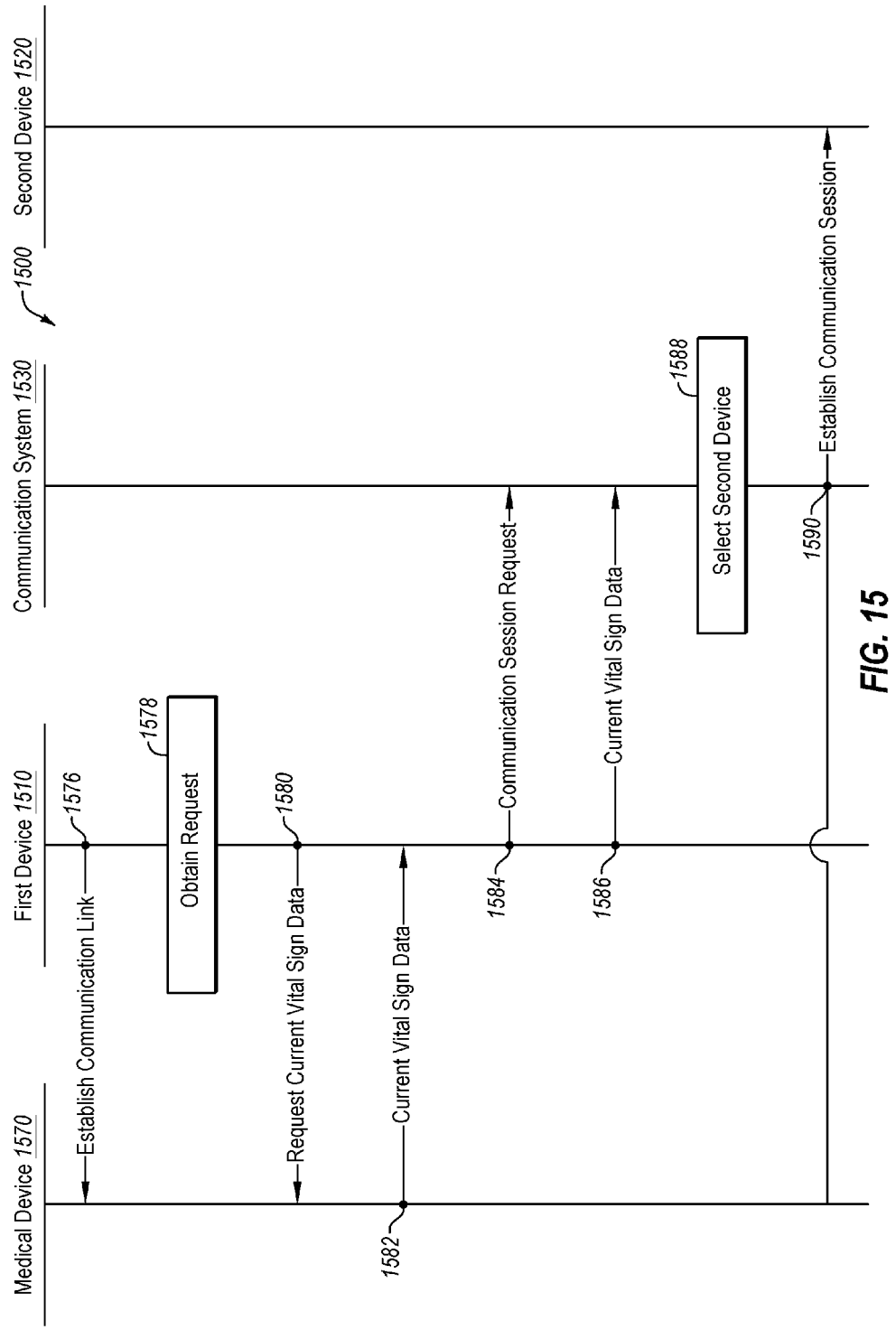
FIG. 15 illustrates example operations in establishment of a communication session between devices.

FIG. 15 illustrates example operations 1500 in establishment of communication between devices. The operations 1500 may be arranged in accordance with at least one embodiment described in the present disclosure. The operations 1500 may be between a first device 1510, a second device 1520, a communication system 1530, and a medical device 1570. In some embodiments, the first device 1510, the second device 1520, the communication system 1530, and the medical device 1570 may be analogous to the first device 1110, one of the second devices 1120, the communication system 1130, and the medical device 1170, respectively, of FIG. 11. Accordingly, no further explanation is provided with respect thereto.

In some embodiments, the operations 1500 may be an example of communications and interactions between the first device 1510, the second device 1520, the communication system 1530, and the medical device 1570 that may occur over one or more networks. The operations 1500 illustrated are not exhaustive but are merely representative of operations 1500 that may occur. Furthermore, one operation as illustrated may represent one or more communications, operations, and/or data exchanges. The operations 1500 generally relate to handling a communication request by the first device 1510 for a communication session with the second device 1520.

At an operation 1576, the first device 1510 may establish a communication link with the medical device 1570. In some embodiments, the first device 1510 may establish a communication link over a local area network, such as a Bluetooth wireless network, 802.11 wireless network, or some other local wireless network configuration.

At operation 1578, the first device 1510 may obtain a request from a user of the first device 1510 to send a request for a communication session to the communication system 1530. In some embodiments, the user may interact with first device 1510 such that the first device 1510 obtains the request. For example, the user may select an icon or element in a user interface or select a button to direct the first device 1510 to request a communication session.

At the operation 1580, the first device 1510 may send a request for current vital sign data to the medical device 1570. The operation 1580 may occur in response to the request from the user obtained in operation 1578. In some embodiments, the request may be sent over the established communication link between the first device 1510 and the medical device 1570 over the local area network. In some embodiments, the first device 1510 may request current vital sign data for every type of vital sign data collected by the medical device 1570. Alternatively or additionally, the first device 1510 may request current vital sign data for a subset of the vital sign data collected by the medical device 1570.

At operation 1582, the medical device 1570 may provide the current vital sign data to the first device 1510. The medical device 1570 may provide the current vital sign data in response to the request for the vital sign data from the first device 1510. In some embodiments, the medical device 1570 may gather data from one or more sensors to generate current vital sign data before sending the current vital sign data to the first device 1510. Alternatively or additionally, the medical device 1570 may send the vital sign data last gathered from the one or more sensors of the medical device 1570.

At operation 1584, the first device 1510 may send a request for a communication session to the communication system 1530. The operation 1584 may occur in response to the request from the user obtained in operation 1578. The request for the communication session may be sent over a wide area network, which may include the Internet. The wide area network may be different than the local area network. In some embodiments, the request for the communication session may be sent to a communication address of the communication system 1530.

At operation 1586, the first device 1510 may send the current vital sign data to the communication system 1530. The operation 1586 may occur in response to the request from the user obtained in operation 1578. The vital sign data may be sent to a different communication address of the communication system 1530 than the request for the communication session. For example, the vital sign data may be sent to a first endpoint in the communication system 1530 and the request for the communication session may be sent to a second endpoint of the communication system 1530. The communication system 1530 may associate the current vital sign data with the user of the first device 1510 and thus any request for a communication session from the first device 1510.

At operation 1588, the communication system 1530 may select the second device 1520 for the communication session with the first device 1510. In some embodiments, the communication system 1530 may select the second device 1520 based on the current vital sign data received from the first device 1510. Additionally or alternatively, the communication system 1530 may select the second device according to one or more operations described above with respect to methods 1200, 1300, and/or 1400 described above with respect to FIGS. 12a and 12b, 13, and 14, respectively.

At operation 1590, the communication system 1530 may establish the communication session between the first device 1510 and the second device 1520 selected based on the current vital sign obtained from the first device 1510.

Modifications, additions, or omissions may be made to the operations 1500 without departing from the scope of the present disclosure. For example, in some embodiments, the operations 1500 may not include one or more of the operations. For example, the operations 1500 may not include the operation 1576. In some embodiments, the operations 1500 may include additional operations. As another example, in some embodiments, the operations 1500 may be arranged in a different order. For example, the operation 1576 may occur after the operation 1578. In these and other embodiments, the operation 1576 may occur in response to the request obtained from the first user. Alternatively or additionally, the operation 1586 may occur before the operation 1584.

Figure 16:
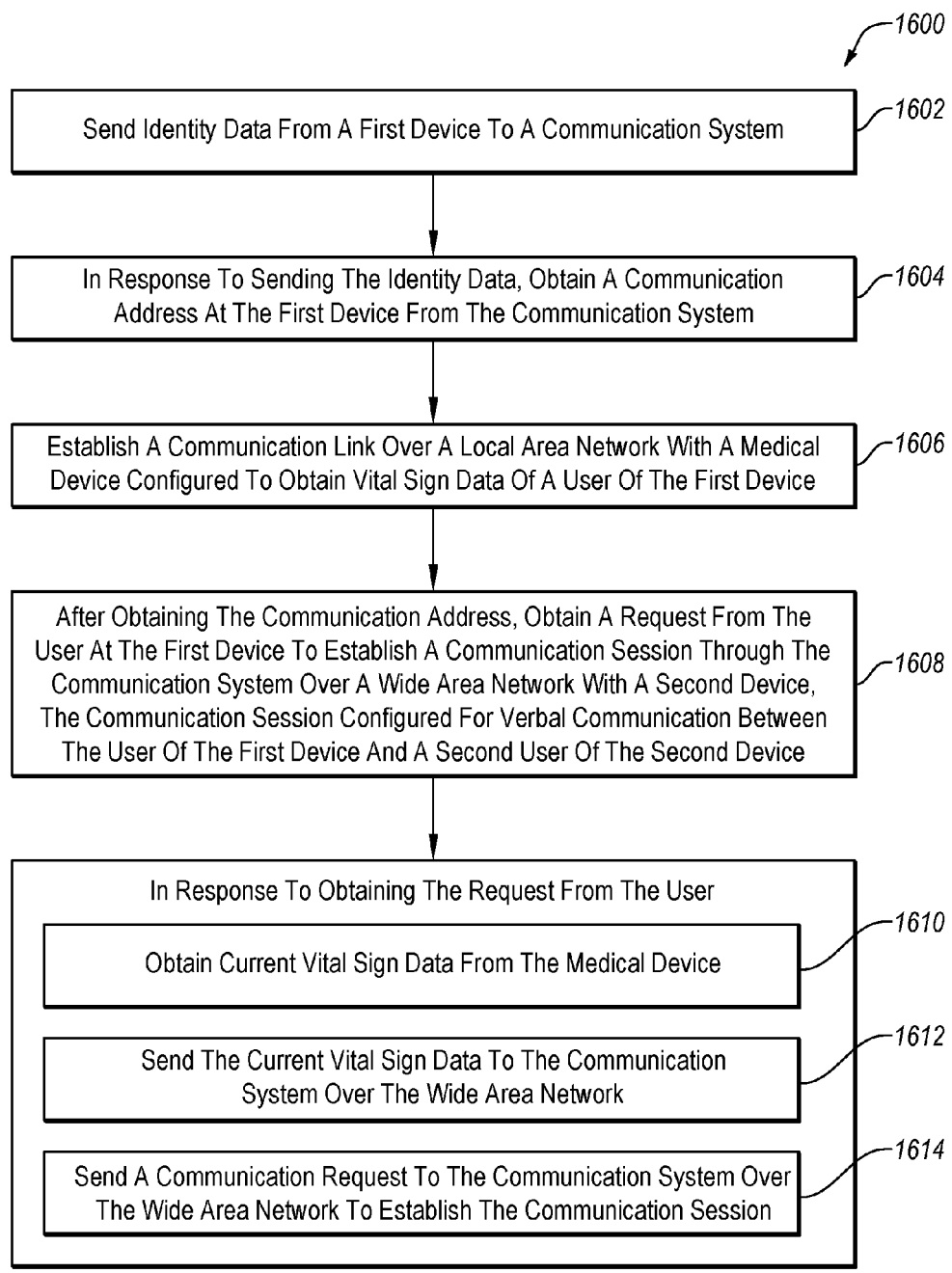
FIG. 16 is a flowchart of an example method to establish communication between devices.

FIG. 16 is a flowchart of an example method 1600 to establish communication between devices. The method 1600 may be arranged in accordance with at least one embodiment described in the present disclosure. The method 1600 may be performed, in whole or in part, in some embodiments by a system, such as the first device 110, 510, 1110, and the system 1700 of FIGS. 1, 5, 11, and 17, respectively. In these and other embodiments, some or all of the operations of the method 1600 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 1600 may begin at block 1602, where identity data is sent from a first device to a communication system. In block 1604, in response to sending the identity data, a communication address may be obtained at the first device from the communication system.

In block 1606, a communication link may be established over a local area network with a medical device configured to obtain vital sign data of a user of the first device.

In block 1608, after obtaining the communication address, a request may be obtained from the user at the first device to establish a communication session through the communication system over a wide area network with a second device. The communication session may be configured for verbal communication between the user of the first device and a second user of the second device. In some embodiments, the communication session may be a video communication session configured for sharing video and audio between the first device and the second device.

In the method 1600, the blocks 1610, 1612, and 1614 may occur in response to obtaining the request from the user.

In block 1610, current vital sign data may be obtained from the medical device. In some embodiments, the current vital sign data includes one or more of: a heart rate, a respiration rate, a temperature, and blood pressure of the user.

In block 1612, the current vital sign data may be sent to the communication system over the wide area network. In some embodiments, the wide area network may include the Internet.

In block 1614, a communication request may be sent to the communication system over the wide area network to establish the communication session. In some embodiments, the current vital sign data is sent to the communication system separately from the communication request. In some embodiments, the communication link may be established over the local area network with the medical device in response to obtaining the request from the user.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 1600 may further include obtaining the communication request and the current vital sign data at the communication system. In some embodiments, the method 1600 may further include selecting, by the communication system, the second device from among multiple second devices to participate in the communication session based on the current vital sign data and establishing, by the communication system, the communication session between the first device and the second device.

In some embodiments, the current vital sign data is provided to a database system of the communication system and the communication request is sent to a routing system of the communication system. In these and other embodiments, the method 1600 may further include requesting, by the routing system, the current vital sign data from the database system in response to obtaining the communication request at the routing system.

Figure 17:
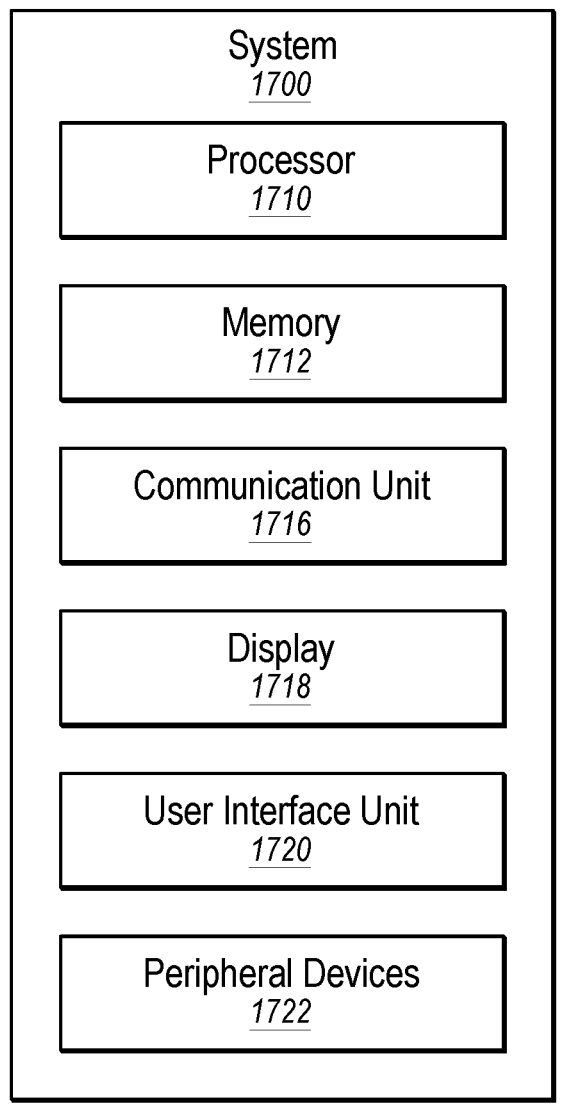
FIG. 17 illustrates an example computing system that may be used to establish or maintain communication sessions between devices, all arranged according to one or more embodiments described in the present disclosure.

FIG. 17 illustrates an example computing system 1700 that may be used to establish or maintain communication sessions between devices. The system 1700 may be arranged in accordance with at least one embodiment described in the present disclosure. The system 1700 may include a processor 1710, a memory 1712, a communication unit 1716, a display 1718, a user interface unit 1720, and a peripheral device 1722, which all may be communicatively coupled. In some embodiments, the system 1700 may be part of any of the systems or devices described in this disclosure.

For example, the system 1700 may be part of the first device 110, 510, and/or 1110 of FIGS. 1, 5, and 11, respectively. In these and other embodiments, the system 1700 may be configured to perform one or more of the following tasks: obtain input from a user, send a request for a communication session to a communication system, participate in a communication session by sending and capturing audio and video of a first user, receive and present audio and video of a second user, receive and present transcript data of the audio of the second user, and obtain vital signs from a medical device and send the vital signs to the communication session, among other tasks described in the present disclosure.

As another example, the system 1700 may be part of the second devices 120, 520, and/or 1120 of FIGS. 1, 5, and 11, respectively. In these and other embodiments, the system 1700 may be configured to perform one or more of the following tasks: receive a request for a communication session, participate in a communication session by sending and capturing audio and video of a second user, receive and present audio and video of a first user, and receive and present transcript data of the audio of the first user, among other tasks described in the present disclosure.

As another example, the system 1700 may be part of the communication system 130, 530, and/or 1130 of FIGS. 1, 5, and 11, respectively, or part of any element described as part of the communication system 130, 530, and/or 1130 of FIGS. 1, 5, and 11, respectively. In these and other embodiments, the system 1700 may be configured to perform one or more of the following tasks: receive a request for a communication session from a first device, obtain profile data and vital sign data, select a second device to participate in the communication session, establish a communication session between the first device and the selected second device, generate transcript data of audio from the first device and the second device, provide the transcript data to the first device and the second device, combine the first and second transcript data, and update the profile data, among other tasks described in the present disclosure.

Generally, the processor 1710 may include any suitable special-purpose or general-purpose computer, computing entity, or processing device including various computer hardware or software modules and may be configured to execute instructions stored on any applicable computer-readable storage media. For example, the processor 1710 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 17, it is understood that the processor 1710 may include any number of processors distributed across any number of networks or physical locations that are configured to perform individually or collectively any number of operations described herein. In some embodiments, the processor 1710 may interpret and/or execute program instructions and/or process data stored in the memory 1712. In some embodiments, the processor 1710 may execute the program instructions stored in the memory 1712.

For example, the system 1700 may be part of the communication system 130, 530, and/or 1130 of FIGS. 1, 5, and 11, respectively. In these and other embodiments, instructions may be used to perform one or more of the methods 300, 400, 800, 900, 1000, 1200, 1300, 1400 of FIGS. 3, 4, 8, 9, 10, 12, 13, and 14, respectively.

As another example, the system 1700 may be part of the first device 110, 510, and/or 1110 of FIGS. 1, 5, and 11, respectively. In these and other embodiments, the instructions may be used to perform the method 1600 of FIG. 16.

The memory 1712 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 1710. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 1710 to perform a certain operation or group of operations as described in this disclosure.

The communication unit 1716 may include any component, device, system, or combination thereof that is configured to transmit or receive information over a network. In some embodiments, the communication unit 1716 may communicate with other devices at other locations, the same location, or even other components within the same system. For example, the communication unit 1716 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, etc.), and/or the like. The communication unit 1716 may permit data to be exchanged with a network and/or any other devices or systems described in the present disclosure. For example, if the system 1700 is included in the first device 110, 510, and/or 1110 of FIGS. 1, 5, and 11, the communication unit 1716 may allow the first device 110, 510, and/or 1110 to communicate with a medical device or a communication system.

The display 1718 may be configured as one or more displays, like an LCD, LED, or other type of display. The display 1718 may be configured to present video, text captions, user interfaces, and other data as directed by the processor 1710. For example, when the system 1700 is included in the first device 110, 510, and/or 1110 of FIGS. 1, 5, and 11, the display 1718 may be configured to present second video from a second device and a transcript of second audio from the second device.

The user interface unit 1720 may include any device to allow a user to interface with the system 1700. For example, the user interface unit 1720 may include a mouse, a track pad, a keyboard, buttons, and/or a touchscreen, among other devices. The user interface unit 1720 may receive input from a user and provide the input to the processor 1710.

The peripheral devices 1722 may include one or more devices. For example, the peripheral devices may include a microphone, an imager, and/or a speaker, among other peripheral devices. In these and other embodiments, the microphone may be configured to capture audio. The imager may be configured to capture digital images. The digital images may be captured in a manner to produce video or image data. In some embodiments, the speaker may broadcast audio received by the system 1700 or otherwise generated by the system 1700. Modifications, additions, or omissions may be made to the system 1700 without departing from the scope of the present disclosure.

In some embodiments, the different components, modules, engines, and services described herein may be implemented as objects or processes that execute on a computing system (e.g., as separate threads). While some of the systems and methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A computer-implemented method to establish communication between devices, the method comprising:
    sending identity data from a first device to a communication system;
    in response to sending the identity data, obtaining a communication address at the first device from the communication system;
    establishing a communication link over a local area network with a medical device configured to obtain vital sign data of a user of the first device;
    after obtaining the communication address, obtaining a request from the user at the first device to establish a communication session through the communication system over a wide area network with a second device, the communication session configured for verbal communication between the user of the first device and a second user of the second device; and
    in response to obtaining the request from the user:
        obtaining current vital sign data from the medical device;
        sending the current vital sign data to the communication system over the wide area network; and
        sending a communication request to the communication system over the wide area network to the communication address to establish the communication session.

2. The method of claim 1, wherein the current vital sign data is sent to the communication system separately from the communication request.

3. The method of claim 1, further comprising participating in the communication session established by the communication system between the first device and a second device, wherein the second device is selected by the communication system from among a plurality of second devices to participate in the communication session based on the current vital sign data provided to the communication system.

4. The method of claim 3, wherein the current vital sign data is provided to a database system of the communication system and the communication request is sent to a routing system of the communication system, the method further comprising in response to obtaining the communication request at the routing system, requesting, by the routing system, the current vital sign data from the database system.

5. The method of claim 1, wherein the local area network includes a Bluetooth network.

6. The method of claim 1, wherein the communication link is established over the local area network with the medical device in response to obtaining the request from the user.

7. The method of claim 1, wherein the current vital sign data includes one or more of: a heart rate, a respiration rate, a temperature, and blood pressure of the user.

8. The method of claim 1, wherein the communication session is a video communication session configured for sharing video and audio between the first device and the second device.

9. One or more non-transitory media configured to store instructions that in response to being executed by one or more processors cause the first device to perform the method of claim 1.

10. A computer-implemented method to establish communication between devices, the method comprising:
    obtaining a request from a user at a first device to establish a communication session through a communication system over a wide area network with a second device, the communication session providing for verbal communication between the user of the first device and a second user of the second device;

obtaining, at the first device over a local area network, current vital sign data of the user from a medical device configured to obtain vital sign data of the user;

in response to the request from the user, sending a communication request to the communication system over the wide area network to establish the communication session; and in response to the request from the user, sending the current vital sign data to the communication system over the wide area network.

11. The method of claim 10, wherein the current vital sign data includes one or more of: a heart rate, a respiration rate, a temperature, and blood pressure of the user.

12. The method of claim 10, further comprising participating in the communication session established by the communication system between the first device and a second device,
wherein the second device is selected by the communication system from among a plurality of second devices to participate in the communication session based on the current vital sign data provided to the communication system.

13. The method of claim 10, wherein a communication link is established over the local area network with the medical device in response to obtaining the request from the user.

14. The method of claim 10, wherein the current vital sign data is sent to the communication system separately from the communication request.

15. One or more non-transitory media configured to store instructions that in response to being executed by one or more processors cause the first device to perform the method of claim 10.

16. A device comprising:
a user interface configured to receive user input to establish a communication session through a communication system over a wide area network with a second device, the communication session providing for verbal communication between a user of the device and a second user of the second device; and
a communication unit configured to:
obtain, over a local area network, current vital sign data of the user from a medical device configured to obtain vital sign data of a user of the device;
in response to the user input from the user to establish a communication session, send a communication request to the communication system over the wide area network to establish the communication session; and
in response to the user input from the user to establish a communication session, send the current vital sign data to the communication system over the wide area network.

17. The device of claim 16, wherein the current vital sign data includes one or more of: a heart rate, a respiration rate, a temperature, and blood pressure of the user.

18. The device of claim 16, wherein the communication unit is further configured to obtain video captured at a second device in the communication session established by the communication session, wherein the device further comprises a display configured to present the video.

19. The device of claim 16, wherein a communication link is established over the local area network with the medical device in response to the user input from the user to establish a communication session.

20. The device of claim 16, wherein the current vital sign data is sent to the communication system separately from the communication request.

* * * * *